(12) United States Patent
Moore et al.

(10) Patent No.: US 8,575,843 B2
(45) Date of Patent: Nov. 5, 2013

(54) SYSTEM, METHOD AND APPARATUS FOR GENERATING PLASMA

(75) Inventors: Cameron A. Moore, Loveland, CO (US); Douglas A. Scott, Laporte, CO (US); George J. Collins, Ft. Collins, CO (US)

(73) Assignee: Colorado State University Research Foundation, Fort Collins, CO (US)

(*) Notice: Subject to any disclaimer, the term of this patent is extended or adjusted under 35 U.S.C. 154(b) by 200 days.

(21) Appl. No.: 12/995,114

(22) PCT Filed: May 29, 2009

(86) PCT No.: PCT/US2009/045733
§ 371 (c)(1),
(2), (4) Date: Feb. 25, 2011

(87) PCT Pub. No.: WO2009/146439
PCT Pub. Date: Dec. 3, 2009

(65) Prior Publication Data
US 2011/0140607 A1    Jun. 16, 2011

Related U.S. Application Data

(60) Provisional application No. 61/057,396, filed on May 30, 2008, provisional application No. 61/057,663, filed on May 30, 2008.

(51) Int. Cl.
*H05B 31/26* (2006.01)
(52) U.S. Cl.
USPC ............. 315/111.21; 315/111.51; 315/111.91
(58) Field of Classification Search
USPC ...................... 315/111.21–111.91
See application file for complete search history.

(56) References Cited

U.S. PATENT DOCUMENTS

| 438,257 A | 10/1890 | Raquet |
| 2,213,820 A | 9/1940 | Maxson |
| 2,598,301 A | 5/1952 | Rajchman |

(Continued)

FOREIGN PATENT DOCUMENTS

| DE | 3710489 | 11/1987 |
| DE | 4139029 | 6/1993 |

(Continued)

OTHER PUBLICATIONS

U.S. Appl. No. 08/383,162, filed Feb. 3, 1995, Lawrence K. Pacer.

(Continued)

*Primary Examiner* — Tung X Le

(57) ABSTRACT

A plasma generating system, related method and device are disclosed. The plasma generation system includes a plasma generation device, a source of ionizable gas and a driver network. The plasma generation device includes a housing, an electrode, and a resonant circuit. The housing includes a passage defined therein and directs a flow of ionizable gas therethrough. The electrode is coupled to the ionizable gas flowing through the passage of the housing. The resonant circuit includes a capacitor and an inductor connected together in series. The resonant circuit has a resonance frequency and is coupled to the electrode. The resonant circuit receives an AC signal. The driver network provides the AC signal such that the AC signal has a frequency and excites the ionizable gas flowing through the passage of the housing to a plasma.

50 Claims, 16 Drawing Sheets

(56) References Cited

U.S. PATENT DOCUMENTS

| | | | |
|---|---|---|---|
| 3,134,947 A | 5/1964 | Charasz |
| 3,838,242 A | 9/1974 | Goucher |
| 3,903,891 A | 9/1975 | Brayshaw |
| 3,938,525 A | 2/1976 | Coucher |
| 4,010,400 A | 3/1977 | Hollister |
| 4,017,707 A | 4/1977 | Brown et al. |
| 4,143,337 A | 3/1979 | Beaulieu |
| 4,177,422 A | 12/1979 | Deficis et al. |
| 4,181,897 A | 1/1980 | Miller |
| 4,188,426 A | 2/1980 | Auerbach |
| 4,274,919 A | 6/1981 | Jensen et al. |
| 4,337,415 A | 6/1982 | Dürr |
| 4,577,165 A | 3/1986 | Uehara et al. |
| 4,629,887 A | 12/1986 | Bernier |
| 4,629,940 A | 12/1986 | Gagne et al. |
| 4,780,803 A | 10/1988 | Dede Garcia-Santamaria |
| 4,781,175 A | 11/1988 | McGreevy et al. |
| 4,818,916 A | 4/1989 | Morrisroe |
| 4,877,999 A | 10/1989 | Knapp et al. |
| 4,901,719 A | 2/1990 | Trenconsky et al. |
| 4,922,210 A | 5/1990 | Flachenecker et al. |
| 4,956,582 A | 9/1990 | Bourassa |
| 5,025,373 A | 6/1991 | Keyser, Jr. et al. |
| 5,041,110 A | 8/1991 | Fleenor |
| 5,098,430 A | 3/1992 | Fleenor |
| 5,117,088 A | 5/1992 | Stava |
| 5,124,526 A | 6/1992 | Muller et al. |
| 5,135,604 A | 8/1992 | Kumar et al. |
| 5,155,547 A | 10/1992 | Casper et al. |
| 5,159,173 A | 10/1992 | Frind et al. |
| 5,180,949 A | 1/1993 | Durr |
| 5,223,457 A | 6/1993 | Mintz et al. |
| 5,256,138 A | 10/1993 | Burek et al. |
| 5,280,154 A | 1/1994 | Cuomo et al. |
| 5,300,068 A | 4/1994 | Rosar et al. |
| 5,304,279 A | 4/1994 | Coultas et al. |
| 5,320,621 A | 6/1994 | Gordon et al. |
| 5,334,834 A | 8/1994 | Ito et al. |
| RE34,780 E | 11/1994 | Trenconsky et al. |
| 5,383,019 A | 1/1995 | Farrell et al. |
| 5,384,167 A | 1/1995 | Nishiwaki et al. |
| 5,401,350 A | 3/1995 | Patrick et al. |
| 5,449,356 A | 9/1995 | Walbrink et al. |
| 5,449,432 A | 9/1995 | Hanawa |
| 5,505,729 A | 4/1996 | Rau |
| 5,526,138 A | 6/1996 | Sato |
| 5,534,231 A | 7/1996 | Savas |
| 5,556,549 A * | 9/1996 | Patrick et al. ............... 216/61 |
| 5,618,382 A | 4/1997 | Mintz et al. |
| 5,683,366 A | 11/1997 | Eggers et al. |
| 5,688,357 A | 11/1997 | Hanawa |
| 5,697,882 A | 12/1997 | Eggers et al. |
| 5,708,330 A | 1/1998 | Rothenbuhler et al. |
| 5,720,745 A | 2/1998 | Farin et al. |
| 5,733,511 A | 3/1998 | De Francesco |
| 5,810,764 A | 9/1998 | Eggers et al. |
| 5,818,581 A | 10/1998 | Kurosawa et al. |
| 5,841,531 A | 11/1998 | Gliddon |
| 5,843,019 A | 12/1998 | Eggers et al. |
| 5,843,079 A | 12/1998 | Suslov |
| 5,845,488 A | 12/1998 | Hancock et al. |
| 5,849,136 A | 12/1998 | Mintz et al. |
| 5,858,477 A | 1/1999 | Veerasamy et al. |
| 5,865,937 A | 2/1999 | Shan et al. |
| 5,866,985 A | 2/1999 | Coultas et al. |
| 5,892,328 A | 4/1999 | Shang et al. |
| 5,909,086 A | 6/1999 | Kim et al. |
| 5,961,772 A | 10/1999 | Selwyn |
| 5,977,715 A | 11/1999 | Li et al. |
| 6,013,075 A | 1/2000 | Avramenko et al. |
| 6,020,794 A | 2/2000 | Wilbur |
| 6,024,733 A | 2/2000 | Eggers et al. |
| 6,027,601 A | 2/2000 | Hanawa |
| 6,030,667 A | 2/2000 | Nakagawa et al. |
| 6,033,582 A | 3/2000 | Lee et al. |
| 6,036,878 A | 3/2000 | Collins |
| 6,046,546 A | 4/2000 | Porter et al. |
| 6,047,700 A | 4/2000 | Eggers et al. |
| 6,053,172 A | 4/2000 | Hovda et al. |
| 6,063,079 A | 5/2000 | Hovda et al. |
| 6,063,084 A | 5/2000 | Farin |
| 6,063,937 A | 5/2000 | Dlubala et al. |
| 6,066,134 A | 5/2000 | Eggers et al. |
| 6,086,585 A | 7/2000 | Hovda et al. |
| 6,099,523 A | 8/2000 | Kim et al. |
| 6,102,046 A | 8/2000 | Weinstein et al. |
| 6,105,581 A | 8/2000 | Eggers et al. |
| 6,109,268 A | 8/2000 | Thapliyal et al. |
| 6,110,395 A | 8/2000 | Gibson, Jr. |
| 6,113,597 A | 9/2000 | Eggers et al. |
| 6,132,575 A | 10/2000 | Pandumsoporn et al. |
| 6,137,237 A | 10/2000 | MacLennan et al. |
| 6,142,992 A | 11/2000 | Cheng et al. |
| 6,149,620 A | 11/2000 | Baker et al. |
| 6,153,852 A | 11/2000 | Blutke et al. |
| 6,159,208 A | 12/2000 | Hovda et al. |
| 6,170,428 B1 | 1/2001 | Redeker et al. |
| 6,178,918 B1 | 1/2001 | Van Os et al. |
| 6,179,836 B1 | 1/2001 | Eggers et al. |
| 6,182,469 B1 | 2/2001 | Campbell et al. |
| 6,183,469 B1 | 2/2001 | Thapliyal et al. |
| 6,183,655 B1 | 2/2001 | Wang et al. |
| 6,190,381 B1 | 2/2001 | Olsen et al. |
| 6,197,026 B1 | 3/2001 | Farin et al. |
| 6,203,542 B1 | 3/2001 | Ellsberry et al. |
| 6,206,871 B1 | 3/2001 | Zanon et al. |
| 6,207,924 B1 | 3/2001 | Trassy |
| 6,210,402 B1 | 4/2001 | Olsen et al. |
| 6,210,410 B1 | 4/2001 | Farin et al. |
| 6,213,999 B1 | 4/2001 | Platt, Jr. et al. |
| 6,222,186 B1 | 4/2001 | Li et al. |
| 6,224,592 B1 | 5/2001 | Eggers et al. |
| 6,225,593 B1 | 5/2001 | Howieson et al. |
| 6,225,693 B1 | 5/2001 | Miyawaki |
| 6,228,078 B1 | 5/2001 | Eggers et al. |
| 6,228,082 B1 | 5/2001 | Baker et al. |
| 6,228,229 B1 | 5/2001 | Raaijmakers et al. |
| 6,235,020 B1 | 5/2001 | Cheng et al. |
| 6,237,526 B1 | 5/2001 | Brcka |
| 6,238,391 B1 | 5/2001 | Olsen et al. |
| 6,242,735 B1 | 6/2001 | Li et al. |
| 6,248,250 B1 | 6/2001 | Hanawa et al. |
| 6,252,354 B1 | 6/2001 | Collins et al. |
| 6,254,600 B1 | 7/2001 | Willink et al. |
| 6,254,738 B1 | 7/2001 | Stimson et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,270,687 B1 | 8/2001 | Ye et al. |
| 6,277,112 B1 | 8/2001 | Underwood et al. |
| 6,277,251 B1 | 8/2001 | Hwang et al. |
| 6,283,961 B1 | 9/2001 | Underwood et al. |
| 6,287,980 B1 | 9/2001 | Hanazaki et al. |
| 6,291,938 B1 | 9/2001 | Jewett et al. |
| 6,296,636 B1 | 10/2001 | Cheng et al. |
| 6,296,638 B1 | 10/2001 | Davison et al. |
| 6,299,948 B1 | 10/2001 | Gherardi et al. |
| 6,309,387 B1 | 10/2001 | Eggers et al. |
| 6,313,587 B1 | 11/2001 | MacLennan et al. |
| 6,326,584 B1 | 12/2001 | Jewett et al. |
| 6,326,739 B1 | 12/2001 | MacLennan et al. |
| 6,328,760 B1 | 12/2001 | James |
| 6,329,757 B1 | 12/2001 | Morrisroe et al. |
| 6,333,481 B2 | 12/2001 | Augeraud et al. |
| 6,345,588 B1 | 2/2002 | Stimson |
| 6,346,108 B1 | 2/2002 | Fischer |
| 6,348,051 B1 | 2/2002 | Farin et al. |
| 6,353,206 B1 | 3/2002 | Roderick |
| 6,355,032 B1 | 3/2002 | Hovda et al. |
| 6,363,937 B1 | 4/2002 | Hovda et al. |
| 6,365,063 B2 | 4/2002 | Collins et al. |
| 6,375,750 B1 | 4/2002 | Van Os et al. |
| 6,379,351 B1 | 4/2002 | Thapliyal et al. |
| 6,387,088 B1 | 5/2002 | Shattuck et al. |

(56) References Cited

U.S. PATENT DOCUMENTS

| | | |
|---|---|---|
| 6,391,025 B1 | 5/2002 | Weinstein et al. |
| 6,396,214 B1 | 5/2002 | Grosse et al. |
| 6,401,652 B1 | 6/2002 | Mohn et al. |
| 6,409,933 B1 | 6/2002 | Holland et al. |
| RE37,780 E | 7/2002 | Lanzani et al. |
| 6,416,507 B1 | 7/2002 | Eggers et al. |
| 6,416,508 B1 | 7/2002 | Eggers et al. |
| 6,416,633 B1 | 7/2002 | Spence |
| 6,424,099 B1 | 7/2002 | Kirkpatrick et al. |
| 6,424,232 B1 | 7/2002 | Mavretic et al. |
| 6,432,103 B1 | 8/2002 | Ellsberry et al. |
| 6,432,260 B1 | 8/2002 | Mahoney et al. |
| 6,443,948 B1 | 9/2002 | Suslov |
| 6,444,084 B1 | 9/2002 | Collins |
| 6,445,141 B1 | 9/2002 | Kastner et al. |
| 6,459,066 B1 | 10/2002 | Khater et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,464,889 B1 | 10/2002 | Lee et al. |
| 6,464,891 B1 | 10/2002 | Druz et al. |
| 6,468,270 B1 | 10/2002 | Hovda et al. |
| 6,468,274 B1 | 10/2002 | Alleyne et al. |
| 6,471,822 B1 | 10/2002 | Yin et al. |
| 6,474,258 B2 | 11/2002 | Brcka |
| 6,482,201 B1 | 11/2002 | Olsen et al. |
| 6,497,826 B2 | 12/2002 | Li et al. |
| 6,500,173 B2 | 12/2002 | Underwood et al. |
| 6,502,416 B2 | 1/2003 | Kawasumi et al. |
| 6,502,588 B2 | 1/2003 | Li et al. |
| 6,507,155 B1 | 1/2003 | Barnes et al. |
| 6,525,481 B1 | 2/2003 | Klima et al. |
| 6,540,741 B1 | 4/2003 | Underwood et al. |
| 6,544,261 B2 | 4/2003 | Ellsberry et al. |
| 6,565,558 B1 | 5/2003 | Lindenmeier et al. |
| 6,575,968 B1 | 6/2003 | Eggers et al. |
| 6,579,289 B2 | 6/2003 | Schnitzler |
| 6,579,426 B1 | 6/2003 | Van Gogh et al. |
| 6,582,423 B1 | 6/2003 | Thapliyal et al. |
| 6,582,427 B1 | 6/2003 | Goble et al. |
| 6,582,429 B2 | 6/2003 | Krishnan et al. |
| 6,589,237 B2 | 7/2003 | Woloszko et al. |
| 6,589,437 B1 | 7/2003 | Collins |
| 6,595,990 B1 | 7/2003 | Weinstein et al. |
| 6,617,794 B2 | 9/2003 | Barnes et al. |
| 6,624,583 B1 | 9/2003 | Coll et al. |
| 6,625,555 B2 | 9/2003 | Kuan et al. |
| 6,629,974 B2 | 10/2003 | Penny et al. |
| 6,632,193 B1 | 10/2003 | Davison et al. |
| 6,632,220 B1 | 10/2003 | Eggers et al. |
| 6,642,526 B2 | 11/2003 | Hartley |
| 6,646,386 B1 | 11/2003 | Sirkis et al. |
| 6,652,717 B1 | 11/2003 | Hong |
| 6,653,594 B2 | 11/2003 | Nakamura et al. |
| 6,657,594 B2 | 12/2003 | Anderson |
| 6,659,106 B1 | 12/2003 | Hovda et al. |
| 6,663,017 B2 | 12/2003 | Endres et al. |
| 6,685,803 B2 | 2/2004 | Lazarovich et al. |
| 6,712,811 B2 | 3/2004 | Underwood et al. |
| 6,719,754 B2 | 4/2004 | Underwood et al. |
| 6,719,883 B2 | 4/2004 | Stimson |
| 6,723,091 B2 | 4/2004 | Goble et al. |
| 6,726,684 B1 | 4/2004 | Woloszko et al. |
| 6,740,842 B2 | 5/2004 | Johnson et al. |
| 6,746,447 B2 | 6/2004 | Davison et al. |
| 6,763,836 B2 | 7/2004 | Tasto et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,774,569 B2 | 8/2004 | De Vries et al. |
| 6,780,178 B2 | 8/2004 | Palanker et al. |
| 6,780,184 B2 | 8/2004 | Tanrisever |
| 6,781,317 B1 | 8/2004 | Goodman |
| 6,787,730 B2 | 9/2004 | Coccio et al. |
| 6,805,130 B2 | 10/2004 | Tasto et al. |
| 6,806,438 B2 | 10/2004 | Nakano et al. |
| 6,815,633 B1 | 11/2004 | Chen et al. |
| 6,818,140 B2 | 11/2004 | Ding |
| 6,832,996 B2 | 12/2004 | Woloszko et al. |
| 6,837,884 B2 | 1/2005 | Woloszko |
| 6,837,887 B2 | 1/2005 | Woloszko et al. |
| 6,837,888 B2 | 1/2005 | Ciarrocca et al. |
| 6,840,937 B2 | 1/2005 | Van Wyk |
| 6,849,191 B2 | 2/2005 | Ono et al. |
| 6,855,143 B2 | 2/2005 | Davison et al. |
| 6,855,225 B1 | 2/2005 | Su et al. |
| 6,867,859 B1 | 3/2005 | Powell |
| 6,876,155 B2 | 4/2005 | Howald et al. |
| 6,890,332 B2 | 5/2005 | Truckai et al. |
| 6,896,672 B1 | 5/2005 | Eggers et al. |
| 6,896,674 B1 | 5/2005 | Woloszko et al. |
| 6,896,775 B2 | 5/2005 | Chistyakov |
| 6,909,237 B1 | 6/2005 | Park et al. |
| 6,915,806 B2 | 7/2005 | Pacek et al. |
| 6,919,527 B2 | 7/2005 | Boulos et al. |
| 6,920,883 B2 | 7/2005 | Bessette et al. |
| 6,921,398 B2 | 7/2005 | Carmel et al. |
| 6,922,093 B2 | 7/2005 | Kanda |
| 6,924,455 B1 | 8/2005 | Chen et al. |
| 6,929,640 B1 | 8/2005 | Underwood et al. |
| 6,949,096 B2 | 9/2005 | Davison et al. |
| 6,949,887 B2 | 9/2005 | Kirkpatrick et al. |
| 6,958,063 B1 | 10/2005 | Soll et al. |
| 6,974,453 B2 | 12/2005 | Woloszko et al. |
| 6,991,631 B2 | 1/2006 | Woloszko et al. |
| 7,004,941 B2 | 2/2006 | Tvinnereim et al. |
| 7,019,253 B2 | 3/2006 | Johnson et al. |
| 7,046,088 B2 | 5/2006 | Ziegler |
| 7,048,733 B2 | 5/2006 | Hartley et al. |
| 7,070,596 B1 | 7/2006 | Woloszko et al. |
| 7,084,832 B2 | 8/2006 | Pribyl |
| 7,090,672 B2 | 8/2006 | Underwood et al. |
| 7,096,819 B2 | 8/2006 | Chen et al. |
| 7,100,532 B2 | 9/2006 | Pribyl |
| 7,104,986 B2 | 9/2006 | Hovda et al. |
| 7,115,185 B1 | 10/2006 | Gonzalez et al. |
| 7,122,035 B2 | 10/2006 | Canady |
| 7,122,965 B2 | 10/2006 | Goodman |
| 7,131,969 B1 | 11/2006 | Hovda et al. |
| 7,132,620 B2 | 11/2006 | Coelho et al. |
| 7,132,996 B2 | 11/2006 | Evans et al. |
| 7,150,745 B2 | 12/2006 | Stern et al. |
| 7,157,857 B2 | 1/2007 | Brouk et al. |
| 7,160,521 B2 | 1/2007 | Porshnev et al. |
| 7,161,112 B2 | 1/2007 | Smith et al. |
| 7,164,484 B2 | 1/2007 | Takahashi et al. |
| 7,166,816 B1 | 1/2007 | Chen et al. |
| 7,179,255 B2 | 2/2007 | Lettice et al. |
| 7,186,234 B2 | 3/2007 | Dahla et al. |
| 7,189,939 B2 | 3/2007 | Lee et al. |
| 7,189,940 B2 | 3/2007 | Kumar et al. |
| 7,190,119 B2 * | 3/2007 | Patrick et al. ............ 315/111.21 |
| 7,192,428 B2 | 3/2007 | Eggers et al. |
| 7,199,399 B2 | 4/2007 | Chin-Lung et al. |
| 7,201,750 B1 | 4/2007 | Eggers et al. |
| 7,214,280 B2 | 5/2007 | Kumar et al. |
| 7,214,934 B2 | 5/2007 | Stevenson |
| 7,217,268 B2 | 5/2007 | Eggers et al. |
| 7,217,903 B2 | 5/2007 | Bayer et al. |
| 7,220,261 B2 | 5/2007 | Truckai et al. |
| 7,227,097 B2 | 6/2007 | Kumar et al. |
| 7,238,185 B2 | 7/2007 | Palanker et al. |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,271,363 B2 | 9/2007 | Lee et al. |
| 7,275,344 B2 | 10/2007 | Woodmansee, III et al. |
| 7,276,063 B2 | 10/2007 | Davison et al. |
| 7,282,244 B2 | 10/2007 | Schaepkens et al. |
| 7,292,191 B2 | 11/2007 | Anderson |
| 7,297,143 B2 | 11/2007 | Woloszko et al. |
| 7,297,145 B2 | 11/2007 | Woloszko et al. |
| 7,298,091 B2 | 11/2007 | Pickard et al. |

(56) References Cited

U.S. PATENT DOCUMENTS

| | | | |
|---|---|---|---|
| 7,309,843 B2 | 12/2007 | Kumar et al. |
| 7,316,682 B2 | 1/2008 | Konesky |
| 7,318,823 B2 | 1/2008 | Sharps et al. |
| 7,331,957 B2 | 2/2008 | Woloszko et al. |
| 7,353,771 B2 | 4/2008 | Millner et al. |
| 7,355,379 B2 | 4/2008 | Kitamura et al. |
| 7,357,798 B2 | 4/2008 | Sharps et al. |
| 7,361,175 B2 | 4/2008 | Suslov |
| 7,387,625 B2 | 6/2008 | Hovda et al. |
| 7,393,351 B2 | 7/2008 | Woloszko et al. |
| 7,399,944 B2 | 7/2008 | DeVries et al. |
| 7,410,669 B2 | 8/2008 | Dieckhoff et al. |
| 7,419,488 B2 | 9/2008 | Ciarrocca et al. |
| 7,426,900 B2 | 9/2008 | Brcka |
| 7,429,260 B2 | 9/2008 | Underwood et al. |
| 7,429,262 B2 | 9/2008 | Woloszko et al. |
| 7,431,857 B2 | 10/2008 | Shannon et al. |
| 7,435,247 B2 | 10/2008 | Woloszko et al. |
| 7,442,191 B2 | 10/2008 | Hovda et al. |
| 7,449,021 B2 | 11/2008 | Underwood et al. |
| 7,453,403 B2 | 11/2008 | Anderson |
| 7,459,899 B2 | 12/2008 | Mattaboni et al. |
| 7,468,059 B2 | 12/2008 | Eggers et al. |
| 7,480,299 B2 | 1/2009 | O'Keeffe et al. |
| 7,489,206 B2 | 2/2009 | Kotani et al. |
| 7,491,200 B2 | 2/2009 | Underwood |
| 7,498,000 B2 | 3/2009 | Pekshev et al. |
| 7,506,014 B2 | 3/2009 | Drummond |
| 7,507,236 B2 | 3/2009 | Eggers et al. |
| 7,510,665 B2 | 3/2009 | Shannon et al. |
| 7,511,246 B2 | 3/2009 | Morris |
| 7,563,261 B2 | 7/2009 | Carmel et al. |
| 7,566,333 B2 | 7/2009 | Van Wyk et al. |
| 7,589,473 B2 | 9/2009 | Suslov |
| 7,611,509 B2 | 11/2009 | Van Wyk |
| 7,632,267 B2 | 12/2009 | Dahla |
| 7,633,231 B2 | 12/2009 | Watson |
| 7,666,478 B2 | 2/2010 | Paulussen et al. |
| 7,691,101 B2 | 4/2010 | Davison et al. |
| 7,692,389 B2 * | 4/2010 | Kirchmeier | 315/111.21 |
| 7,708,733 B2 | 5/2010 | Sanders et al. |
| 7,715,889 B2 | 5/2010 | Ito |
| 7,758,575 B2 | 7/2010 | Beller |
| 7,824,398 B2 | 11/2010 | Woloszko et al. |
| 7,879,034 B2 | 2/2011 | Woloszko et al. |
| 7,887,891 B2 | 2/2011 | Rius |
| 7,892,223 B2 | 2/2011 | Geiselhart |
| 7,892,230 B2 | 2/2011 | Woloszko |
| 7,901,403 B2 | 3/2011 | Woloszko et al. |
| 7,940,008 B2 | 5/2011 | Mattaboni et al. |
| 7,949,407 B2 | 5/2011 | Kaplan et al. |
| 8,040,068 B2 * | 10/2011 | Coumou et al. | 315/111.21 |
| 8,264,154 B2 * | 9/2012 | Banner et al. | 315/111.71 |
| 2001/0029373 A1 | 10/2001 | Baker et al. |
| 2001/0054601 A1 | 12/2001 | Ding |
| 2002/0022836 A1 | 2/2002 | Goble et al. |
| 2002/0023899 A1 | 2/2002 | Khater et al. |
| 2002/0047543 A1 * | 4/2002 | Sugai et al. | 315/111.21 |
| 2002/0092826 A1 | 7/2002 | Ding |
| 2002/0125207 A1 | 9/2002 | Ono et al. |
| 2002/0132380 A1 | 9/2002 | Nakano et al. |
| 2003/0006019 A1 | 1/2003 | Johnson et al. |
| 2003/0075522 A1 | 4/2003 | Weichart et al. |
| 2003/0084613 A1 | 5/2003 | Futamura et al. |
| 2003/0088245 A1 | 5/2003 | Woloszko et al. |
| 2003/0132198 A1 | 7/2003 | Ono et al. |
| 2003/0158545 A1 | 8/2003 | Hovda et al. |
| 2003/0171743 A1 | 9/2003 | Tasto et al. |
| 2003/0208196 A1 | 11/2003 | Stone |
| 2003/0212396 A1 | 11/2003 | Eggers et al. |
| 2004/0007985 A1 | 1/2004 | De Vries et al. |
| 2004/0086434 A1 | 5/2004 | Gadgil et al. |
| 2004/0112518 A1 | 6/2004 | Rossier et al. |
| 2004/0116922 A1 | 6/2004 | Hovda et al. |
| 2004/0127893 A1 | 7/2004 | Hovda |
| 2004/0129212 A1 | 7/2004 | Gadgil et al. |
| 2004/0230190 A1 | 11/2004 | Dahla et al. |
| 2005/0017646 A1 | 1/2005 | Boulos et al. |
| 2005/0075630 A1 | 4/2005 | Truckai et al. |
| 2005/0264218 A1 * | 12/2005 | Dhindsa et al. | 315/111.21 |
| 2006/0017388 A1 | 1/2006 | Stevenson |
| 2006/0021580 A1 | 2/2006 | Hirano |
| 2006/0036237 A1 | 2/2006 | Davison et al. |
| 2006/0038992 A1 | 2/2006 | Morrisroe |
| 2006/0065628 A1 | 3/2006 | Vahedi et al. |
| 2006/0084158 A1 | 4/2006 | Viol |
| 2006/0095031 A1 | 5/2006 | Ormsby |
| 2006/0175015 A1 | 8/2006 | Chen et al. |
| 2006/0189971 A1 | 8/2006 | Tasto et al. |
| 2006/0189976 A1 | 8/2006 | Karni et al. |
| 2006/0259025 A1 | 11/2006 | Dahla |
| 2006/0266735 A1 | 11/2006 | Shannon et al. |
| 2007/0021747 A1 | 1/2007 | Suslov |
| 2007/0021748 A1 | 1/2007 | Suslov |
| 2007/0029292 A1 | 2/2007 | Suslov |
| 2007/0084563 A1 | 4/2007 | Holland |
| 2007/0087455 A1 | 4/2007 | Hoffman |
| 2007/0093804 A1 | 4/2007 | Kaveckis et al. |
| 2007/0093805 A1 | 4/2007 | Auth et al. |
| 2007/0106288 A1 | 5/2007 | Woloszko et al. |
| 2007/0149966 A1 | 6/2007 | Dahla et al. |
| 2007/0149970 A1 | 6/2007 | Schnitzler et al. |
| 2007/0161981 A1 | 7/2007 | Sanders et al. |
| 2007/0213704 A1 | 9/2007 | Truckai et al. |
| 2007/0251920 A1 | 11/2007 | Hoffman |
| 2007/0258329 A1 | 11/2007 | Winey |
| 2007/7291804 | 11/2007 | Suslov |
| 2007/0290620 A1 | 12/2007 | Lee et al. |
| 2008/0023443 A1 | 1/2008 | Paterson et al. |
| 2008/0039832 A1 | 2/2008 | Palanker et al. |
| 2008/0083701 A1 | 4/2008 | Shao et al. |
| 2008/0089895 A1 | 4/2008 | Utku et al. |
| 2008/0099434 A1 | 5/2008 | Chandrachood et al. |
| 2008/0099435 A1 | 5/2008 | Grimbergen |
| 2008/0099436 A1 | 5/2008 | Grimbergen |
| 2008/0108985 A1 | 5/2008 | Konesky |
| 2008/0138374 A1 | 6/2008 | Storey et al. |
| 2008/0167398 A1 | 7/2008 | Patil et al. |
| 2008/0179290 A1 | 7/2008 | Collins et al. |
| 2008/0185366 A1 | 8/2008 | Suslov |
| 2008/0268172 A1 | 10/2008 | Fukuda et al. |
| 2008/0284506 A1 | 11/2008 | Messer |
| 2008/0292497 A1 | 11/2008 | Vangeneugden et al. |
| 2009/0039789 A1 | 2/2009 | Nikolay |
| 2009/0054896 A1 | 2/2009 | Fridman et al. |
| 2009/0064933 A1 | 3/2009 | Liu et al. |
| 2010/0089742 A1 | 4/2010 | Suslov |
| 2010/0130973 A1 | 5/2010 | Choi et al. |

FOREIGN PATENT DOCUMENTS

| | | |
|---|---|---|
| DE | 4326037 | 2/1995 |
| DE | 9117019 | 4/1995 |
| DE | 19537897 | 3/1997 |
| DE | 9117299 | 4/2000 |
| DE | 19848784 | 5/2000 |
| DE | 29724247 | 8/2000 |
| DE | 19524645 | 11/2002 |
| EP | 0016542 A2 | 10/1980 |
| EP | 0016542 B1 | 10/1980 |
| EP | 0 495 699 B1 | 7/1992 |
| EP | 0602764 A1 | 6/1994 |
| EP | 0956827 | 11/1999 |
| EP | 1174901 A2 | 1/2002 |
| FR | 1340509 | 9/1963 |
| JP | 61-159953 | 7/1986 |
| SU | 1438745 | 11/1988 |
| WO | WO 99/01887 | 1/1999 |
| WO | WO 99/36940 | 7/1999 |
| WO | WO 01/39555 A1 | 5/2001 |
| WO | WO 2006/116252 A1 | 11/2006 |

(56) References Cited

FOREIGN PATENT DOCUMENTS

OTHER PUBLICATIONS

U.S. Appl. No. 08/619,380, filed Mar. 21, 1996, Gene H. Arts.
U.S. Appl. No. 08/621,151, filed Mar. 21, 1996, Robert B. Stoddard.
U.S. Appl. No. 08/878,694, filed Jun. 19, 1997, Lawrence K Pacer.
U.S. Appl. No. 09/270,856, filed Mar. 17, 1999, Gene H. Arts.
U.S. Appl. No. 09/504,640, filed Feb. 16, 2000, James Steven Cunningham.
U.S. Appl. No. 09/666,312, filed Sep. 21, 2000, Robert C. Platt.
U.S. Appl. No. 12/791,100, filed Jun. 1, 2010, Kristin D. Johnson.
U.S. Appl. No. 12/845,842, filed Jul. 29, 2010, Kristin D. Johnson.
U.S. Appl. No. 12/995,106, filed Nov. 29, 2010, Il-Gyo Koo.
U.S. Appl. No. 12/995,114, filed Nov. 29, 2010, Cameron A. Moore.
Hernandez et al., "A Controlled Study of the Argon Beam Coagultor for Partial Nephrectomy"; The Journal of Urology, vol. 143, May (1990) J. Urol. 143: pp. 1062-1065.
Ward et al., "A Significant New Contribution to Radical Head and Neck Surgery"; Arch Otolaryngology, Head and Neck Surg., vol. 115 pp. 921-923 (Aug. 1989).
Lieberman et al., "Capacitive Discharges", Principles of Plasma Discharges and Materials Processing, John Wiley & Son, Inc. (2005) pp. 387-460.
Moore et al., "Confined Geometry Interactions of Downstream RF-Excited Atmospheric Plasma Wires", IEEE Transactions on Plasma Science, 0093-3813, (2008) pp. 1-2.
Walsh et al., "Contrasting Characteristics of Pulsed and Sinusoidal Cold Atmospheric Plasma Jets", Applied Physics Letters, 88, 171501 (2006) pp. 1-3.
Cho et al., "Coplanar ac Discharges Between Cylindrical Electrodes With a Nanoporous Alumina Dielectric: Modular Dielectric Barrier Plasma Devices", IEEE Transactions on Plasma Science, vol. 33, No. 2, (Apr. 2005) pp. 378-379.
Xu et al., "DBD Plasma Jet in Atmospheric Pressure Argon", IEEE Transactions on Plasma Science, vol. 36, No. 4, (Aug. 2008), pp. 1352-1353.
Alfred Grill, "Electron Cyclotron Resonance Plasmas", Cold Plasma in Materials Fabrication, IEEE Press (1994) pp. 40-43.
Brand et al., "Electrosurgical Debulking of Ovarian Cancer: A New Technique Using the Argon Beam Coagulator"; Gynecologic Oncology 39 pp. 115-118 (1990).
Grund et al., "Endoscopic Argon Plasma . . . Flexible Endoscopy"; Endoscopic Surgery and Allied Technologies, No. 1, vol. 2, pp. 42-46 (Feb. 1994).
Waye et al., "Endoscopic Treatment Options"; Techniques in Therapeutic Endoscopy, pp. 1.7-1.15, (1987).
B.D. Cullity, "Introduction to Magnetic Materials", University of Notre Dame; Addison-Wesley Publishing Company, Reading MA., (1972) pp. 23-28.
Brian Chapman, "Matching Networks", Glow Discharge Processes, John Wiley & Sons Inc., NY, (1980) pp. 153-172.
Yin et al., "Miniaturization of Inductively Coupled Plasma Sources", IEEE Transactions on Plasma Science, vol. 27, No. 5, (Oct. 1999) pp. 1516-1524.
Park et al., "Nanoporous Anodic Alumina Film on Glass: Improving Transparency by an Ion-Drift Process", Electrochemical and Solid-State Letters, 8 (3) (2005), pp. D5-D7.
P.A. Tulle, "Off-Resonance Microwave-Created Plasmas", Plasma Physics, Pergamon Press (1973) vol. 15, pp. 971-976.
Lieberman et al., "Ohmic Heating", Principles of Plasma Discharges and Materials Processing, John Wiley & Son, Inc. (2005) pp. 97-98.
Lieberman et al., "Optical Actinometry", Principles of Plasma Discharges and Materials Processing, John Wiley & Son, Inc. (2005) pp. 277-279.
Cho et al., "Ozone Production by Nanoporous Dielectric Barrier Glow Discharge in Atmospheric Pressure Air", Applied Physics Letters, 92, 101504, (2008) pp. 1-3.
Lieberman et al., "Particle and Energy Balance in Discharges", Principles of Plasma Discharges and Materials Processing, John Wiley & Son, Inc. (2005) pp. 329-381.
Woloszko et al., "Plasma Characteristics of Repetitively-Pulsed Electrical Discharges in Saline Solutions Used for Surgical Procedures", IEEE Transactions of Plasma Science, vol. 30, No. 3, (Jun. 2002) pp. 1376-1383.
Stoffels et al., "Plasma Needle for In Vivo Medical Treatment: Recent Developments and Perspectives", Plasma Sources Science and Technology 15 (2006) pp. 169-180.
Schaper et al., "Plasma Production and Vapour Layer Production at a Pulse Power Electrode in Saline Solution:", (2008) www.escampig2008.csic.es/PosterSessions/100.
Akitsu et al., "Plasma Sterilization Using Glow Discharge at Atmospheric Pressure", Surface & Coatings Technology 193, (2005) pp. 29-34.
Koo et al., "Room-temperature Slot Microplasma in Atmospheric Pressure Air Between Cylindrical Electrodes With a Nanoporous Alumina Dielectric", Applied Physics Letters, 91, 041502 (2007) pp. 1-3.
Brian Chapman, "Secondary Electron Emission", Glow Discharge Processes, John Wiley & Sons Inc., NY, (1980) pp. 82-138.
Moore et al., "Sensitive, Nonintrusive, In-Situ Measurement of Temporally and Spatially Resolved Plasma Electric Fields", Physical Review Letters, vol. 52, No. 7, (Feb. 13, 1984) pp. 538-541.
Lieberman et al., "Sheaths", Principles of Plasma Discharges and Materials Processing, John Wiley & Son, Inc. (2005) pp. 11-14.
Farin et al., Technology of Argon Plasma . . . Endoscopic Applications; Endoscopic Surgery and Allied Technologies, No. 1, vol. 2, pp. 71-77 (Feb. 1994).
Lieberman et al., "The Collisionless Sheath", Principles of Plasma Discharges and Materials Processing, John Wiley & Son, Inc. (2005) pp. 167-206.
Gupta et al., "The Potential of Pulsed Underwater Streamer Discharges as a Disinfection Technique", IEEE Transactions on Plasma Science, vol. 36, No. 4, (Aug. 2008) pp. 1621-1632.
Mark H. Mellow, "The Role of Endoscopic Laser Therapy in Gastrointestinal Neoplasms"; Advanced Therapeutic Endoscopy, pp. 17-21, (1990).
Silverstein et al., "Thermal Coagulation Therapy for Upper Gastrointestinal Bleeding"; Advanced Therapeutic Endoscopy, pp. 79-84, 1990.
European Search Report EP 01 10 2843.8, dated May 15, 2001.
European Search Report EP 05 00 2257, dated Jun. 1, 2005.
European Search Report EP 05 01 8087, dated Oct. 17, 2005.
European Search Report EP 06 01 9572 dated Nov. 21, 2006.
European Search Report EP 07 00 4356 dated Jul. 2, 2007.
European Search Report EP 07 00 4659 dated Feb. 19, 2008.
European Search Report EP 07 00 4659—partial dated May 24, 2007.
European Search Report EP 09 00 4975 dated Sep. 11, 2009.
European Search Report EP 09 01 0519 dated Nov. 16, 2009.
European Search Report EP 09 01 0520 dated Dec. 10, 2009.
European Search Report EP 09 01 5212.5 dated Apr. 1, 2010.
European Search Report EP 09 17 1599.5 dated Mar. 16, 2010.
European Search Report EP 09 17 1600.1 dated Jan. 26, 2010.
European Search Report EP 10 174107.2 dated Nov. 5, 2010.
European Search Report EP 10 180 912.7 dated Dec. 8, 2010.
European Search Report EP 10 186524.4 dated Feb. 18, 2011.
International Search Report PCT/US98/19284, dated Jan. 14, 1999.
International Search Report from corresponding EP Appl. No. 09755799.5 mailed Aug. 31, 2012.

* cited by examiner

SYSTEM, METHOD AND APPARATUS FOR GENERATING PLASMA

CROSS-REFERENCE TO RELATED APPLICATION

The present application claims the benefit of and priority to U.S. Provisional Application Ser. No. 61/057,396 entitled "RESONANT EXCITED PLASMA JET DEVICE" filed by Scott et al. on May 30, 2008 and U.S. Provisional Application Ser. No. 61/057,663 entitled "SYSTEM AND METHOD FOR CONTROLLING ELECTROSURGICAL GENERATOR" filed by Moore on May 30, 2008, the entire contents of each of these applications are hereby incorporated by reference herein.

BACKGROUND

1. Technical Field

The present disclosure relates to medical devices. More particularly, the present disclosure relates to a system, method, and apparatus for generating plasma, e.g., for tissue modification in a selective manner.

2. Background of Related Art

Electrical discharges in gaseous and liquid media ("plasmas") have broad applicability to provide alternative solutions to industrial, scientific and medical needs. Plasmas have the unique ability to create large amounts of ions, electrons, radicals, and excited-state (e.g., metastable) species with which to perform material property changes with high spatial and temporal control. Plasmas are also capable of generating practical amounts of photons (to act as a light source including lasers), and unique chemical species and radicals that can both be used to drive non-equilibrium or selective chemical reactions.

Plasmas are commonly generated using electrical energy that is delivered as either (a) direct current (DC) electricity or (b) electricity that is alternating (AC) at frequencies from a single hertz (Hz) to gigahertz (GHz), including the radio frequency ("RF", 0.1 to 100 MHz) and microwave ("MW", 0.1 to 100 GHz) bands, using appropriate generators, electrodes and antennas. Choice of excitation frequency determines many properties and requirements of both the plasma as well as the electrical circuit that is used to deliver electrical energy to the circuit. The performance of the plasma and the design of the electrical excitation circuitry are strongly interrelated.

SUMMARY

The present disclosure relates to a system, method, and apparatus for generating plasma. In one embodiment of the present disclosure, a plasma generating system includes a plasma generation device, a source of ionizable gas, and a driver network. In one illustrative embodiment, the plasma generation device is implemented as a medical device. The plasma generation device includes a housing, an electrode, and a resonant circuit. The housing includes a passage defined therein and directs a flow of ionizable gas therethrough. The electrode is coupled (e.g., capacitively coupled) to the ionizable gas flowing through the passage of the housing. The resonant circuit has a resonance frequency and is electrically coupled to the electrode. The resonant circuit receives an AC signal. The driver network provides the AC signal such that the AC signal has a frequency and excites the ionizable gas flowing through the passage of the housing to a plasma. The driver network can provide an AC signal having a frequency near to the resonance frequency of the resonant circuit, to match an internal impedance of the driver network to an impedance of the resonant circuit both with and without the plasma ignited, and/or maintaining operation within a bandwidth, e.g., a predetermined bandwidth.

In another embodiment of the present disclosure, a plasma-generating device includes a housing including a passage defined therein. The passage is configured to direct a flow of ionizable gas therethrough. The plasma-generating device includes an electrode coupled (e.g., capacitively coupled) to the ionizable gas flowing through the passage of the housing. The plasma-generating device also includes a resonant circuit having an excitation at a resonance frequency electrically coupled to the electrode. The resonant circuit receives an AC signal having a frequency and magnitude configured to excite the ionizable gas flowing through the passage of the housing generating a plasma. The passage may be defined by a quartz or ceramic tube. The plasma-generating device may have a grounding electrode adapted to couple the ionizable gas to a ground. Additionally or alternatively, the electrode is adapted to provide a capacitance and the inductor is electrically coupled to the capacitance of the electrode substantially defining the resonance frequency of the resonant circuit as well as its bandwidth.

In yet another embodiment of the present disclosure, a method includes providing a providing a fluid path configured to direct a flow of ionizable gas and providing a resonant circuit having a resonance frequency electrically coupled to an AC signal. The resonant circuit is coupled (e.g., capacitively coupled) to the ionizable gas flowing within the fluid path. The method also determines a frequency and/or a magnitude of the AC signal to drive the resonant circuit to excite the ionizable gas and applies the AC signal to the resonant circuit thereby exciting the ionizable gas to a plasma.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1A:
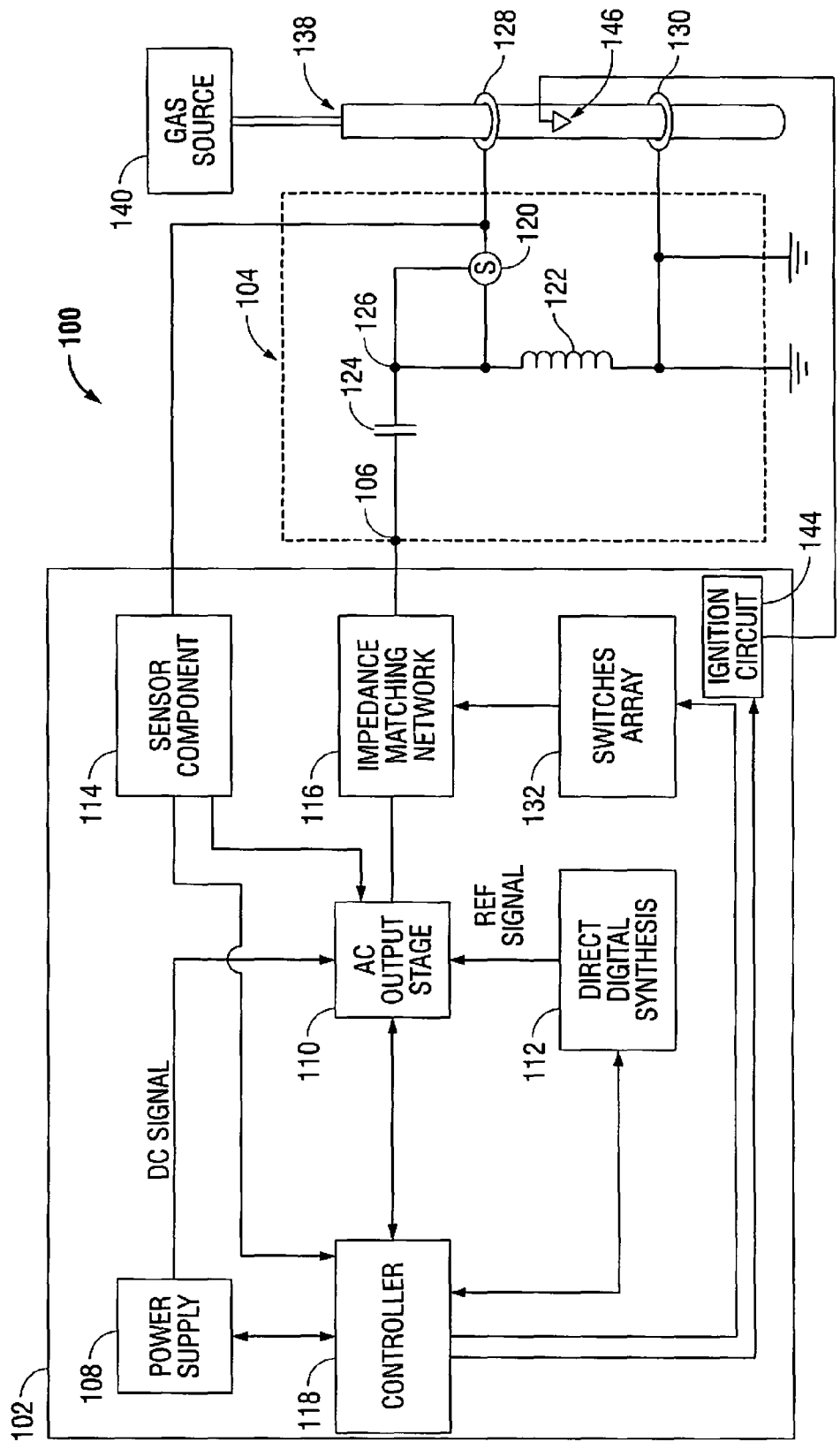
FIG. 1A is a schematic diagram of a plasma generation system in accordance with an embodiment of the present disclosure.

Referring to the drawings, FIG. 1A shows a schematic diagram of a plasma generation system 100, in accordance with an embodiment of the present disclosure. Plasma generation system 100 includes a driver network 102 and a resonant circuit 104. Driver network 102 electrically cooperates with resonant circuit 104 to generate plasma. Driver network 102 is electrically coupled to resonant circuit 104 and electrically communicates an alternating current ("AC") signal thereto through node 106. Driver network 102 provides the AC signal such that the AC signal is at or near the resonant frequency of circuit 104. The frequency of the AC signal is discussed in more detail below.

The plasma generation system 100 can generate plasma at modest power levels such as two watts, one's of watts, or ten's of watts, and can generate what is commonly referred to as cold plasma. In one embodiment of the present disclosure, plasma generation system 100 generates cold plasma having ionization within approximately the range from about $1*10^{-7}$ to about $1*10^{-4}$. The cold plasma may be in non-thermal equilibrium with the rotational temperature being lower than about 100 degrees Celsius or lower than 50 degrees Celsius. The rotational temperature of the cold plasma may be substantially lower than the vibrational temperature of the cold plasma. In other embodiments, the ionizable gas may be cooled such that the ion temperature of the cold plasma is below room temperature. The plasma may be used for selective surface modification in tissue processing such that an upper layer can be removed without damaging an underlayer utilizing selective chemistry or particle bombardment or both.

Driver network 102 provides the AC signal having sufficient voltage, current, frequency and internal impedance such that resonant circuit 104 generates plasma. Driver network 102 includes a power supply 108, an AC output stage 110, a direct digital synthesis device 112, a sensor component 114, an impedance matching network 116, an ignition circuit 144 and a controller 118. Controller 118 controls driver network 102 and the AC signal supplied to node 106. Power supply 108 supplies power using a DC signal to driver network 102 including AC output stage 110. AC output stage 110 converts the DC signal from power supply 108 to the AC signal supplied to node 106 through impedance matching network 116 using a reference signal from direct digital synthesis device 112. Sensor component 114 receives data from sensor 120 and communicates the data to controller 118.

Controller 118 may be a microprocessor, a microcontroller, a Field Programmable Gate array, a programmable logic device, and the like. Controller 118 may implement a control algorithm in any combination of hardware, software, software in execution, firmware, and the like. For example, controller 118 may control the AC signal supplied to node 106 via impedance matching network 116 utilizing one or more Proportional-Integral-Derivative control algorithms. The Proportional-Integral-Derivative control algorithms may control the frequency, current, voltage, bandwidth, pulsing, and/or the duty cycle of the AC signal supplied to resonant circuit 104, or some combination thereof. For example, controller 118 may send a pulse-width modulated signal to power supply 108 to control the voltage of the DC signal supplied to AC output stage 110; controlling the DC signal supplied to AC output stage 110 also controls the source to gate bias voltage of one or more switching MOSFETs of AC output stage 110. The rail voltage between the source and drain voltage of one or more switching MOSFETs controls the peak voltage of the AC signal provided by AC output stage 110. Additionally or alternatively, controller 118 may supply a separate DC signal to set an amplifier gain (not explicitly shown) on AC output stage 110. Controller 118 may control for phase, impedance, voltage, current, power, and the like (described in more detail below).

Driver network 102 includes a power supply 108. Power supply 100 supplies power to driver network 102 using a DC signal. Power supply 108 may be an AC-to-DC converter, a DC-to-DC converter, a switched-mode power supply and the like. Power supply 108 may be controlled via a pulse width modulated signal from controller 118, utilizing an internal self-regulated voltage or current reference. For example, power supply 108 receives an AC signal from a wall outlet, rectifies the AC signal to an unregulated DC signal, and regulates the unregulated DC signal for output using a buck-boost converter. The DC signal supplied by power supply 108 may be used as a bias voltage to a switching device in AC output stage 110. The switches may be controlled using a reference signal from direct digital synthesis device 112.

Direct digital synthesis device 112 generates a reference signal supplied to AC output stage 110. The reference signal may have the same frequency as the AC signal supplied to resonant circuit 104, or a multiple or fraction thereof. The reference signal may be a switching signal supplied to AC output stage 110 to switch one or more MOSFETs therein. Direct digital synthesis device 112 is controlled by controller 118. Controller 118 may control the frequency of the reference signal by digitally communicating a frequency or a phase increment value to a frequency or a phase increment register of direct digital synthesis device 112. Direct digital synthesis device 112 may have a Digital-to-Analog conversion resolution of about 3kHz to about 10 kHz per binary step or lower. In alternative embodiments, a voltage controlled oscillator, a clock, a numerically controlled oscillator, and the like may be used to generate the reference signal.

Driver network 102 may also include an ignition circuit 144 electrically coupled to needle electrode 146. Controller 118 may utilize sensor 120 to detect if/when the plasma is extinguished (e.g., when the plasma current goes to about or equal to zero amps). Once controller 118 determines that plasma is no longer being generated, ignition circuit 114 may apply an electrical signal to needle electrode 146 to assist in the ignition of plasma. Ignition circuit 114 may include one or more switches to selectively connect an electrical signal to the needle electrode 146.

Resonant circuit 104 receives the AC signal from driver network 102 to generate plasma. Resonant circuit includes an inductor 122 and a capacitor 124 connected serially together at node 126. Inductor 122 and a capacitor 124 may be configured in either order. Inductor 122 may be shielded or unshielded. Resonant circuit 104 has a resonant frequency that may include one or more capacitors, represented by capacitor 124, in series with one or more inductors, represented by inductor 122. Additionally or alternatively, capacitor 124 may also be a lumped-element model modeling the capacitance from a physical capacitive device (e.g., a capacitor), capacitance caused by the generated plasma, capacitance by electrodes 128 and 130 (discussed below), and any parasitic capacitances. For example, capacitor 124 may include a physical 5 picofarads capacitor and any capacitance caused by the generated plasma.

Resonant circuit 104 includes electrodes 128 and 130. Electrodes 128 and/or 130 are copper circular strips of metal and are disposed around a quart tube 138. Electrodes 128 and/or 130 may be any suitable geometry and material. The electrodes 128 and/or 130 are disposed around quartz tube 138 and form a capacitive couple to the ionizable gas flowing therein. In some embodiments, quartz tube 138 may be made from a ceramic, a dielectric material, an insulating material, and/or other suitable material. Plasma is generated by the capacitive coupling of resonant circuit 104 to an ionizable gas, e.g., argon, helium and other noble gases. Resonant circuit 104 is capacitively coupled to the ionizable gas via electrode 128. Ionizable gas is received within tube 138 from gas source 140. Electrode 128 is electrically coupled to the electrical energy by node 126. Also, an electrode 130 may be grounded to prevent a "shifting" (sometimes referred to as a "floating") ground. As shown, electrode 128 is "upstream" of a work piece (not shown), while electrode 130 is "downstream" towards the work piece (not shown). The electrical energy from resonant circuit 104 is transferred to the ionizable gas utilizing electrodes 128 and 130 to transform at least a portion of the ionizable gas to a plasma state such as a cold plasma state.

After ignition, capacitor 124 will increase due to the additional capacitance of the generated plasma, e.g., resonant circuit 102 may include an additional 20 picofarads to 120 picofarads due to the capacitance of the generated plasma primarily because of its geometry overlap with respect to the electrodes. The additional impedance (e.g., capacitance and resistance) can cause the resonance frequency of resonant circuit 104 to shift or change. Resonant circuit 104 may have multiple resonance frequencies which change or shift when the plasma is ignited. As mentioned previously, resonant circuit 104 is capacitively coupled to the ionizable gas to generate the plasma. In resonant circuit 104, capacitor 124 and inductor 122 may be interchanged. Resonant circuit 104 receives an AC signal from driver network 102 such that the AC signal and the resonant circuit 104 are driven at an excitation frequency suitable for excitation of the ionizable gas. Additionally or alternatively, the frequency of driver network 102 may be at or near the ion plasma frequency or the electron-atom collision frequency to control either bias voltages from the plasma to the surface or bulk plasma properties. The ion plasma frequency is the frequency where ions in the plasma have a decreasing ability to mechanically respond to the changing frequency.

Figure 1B:
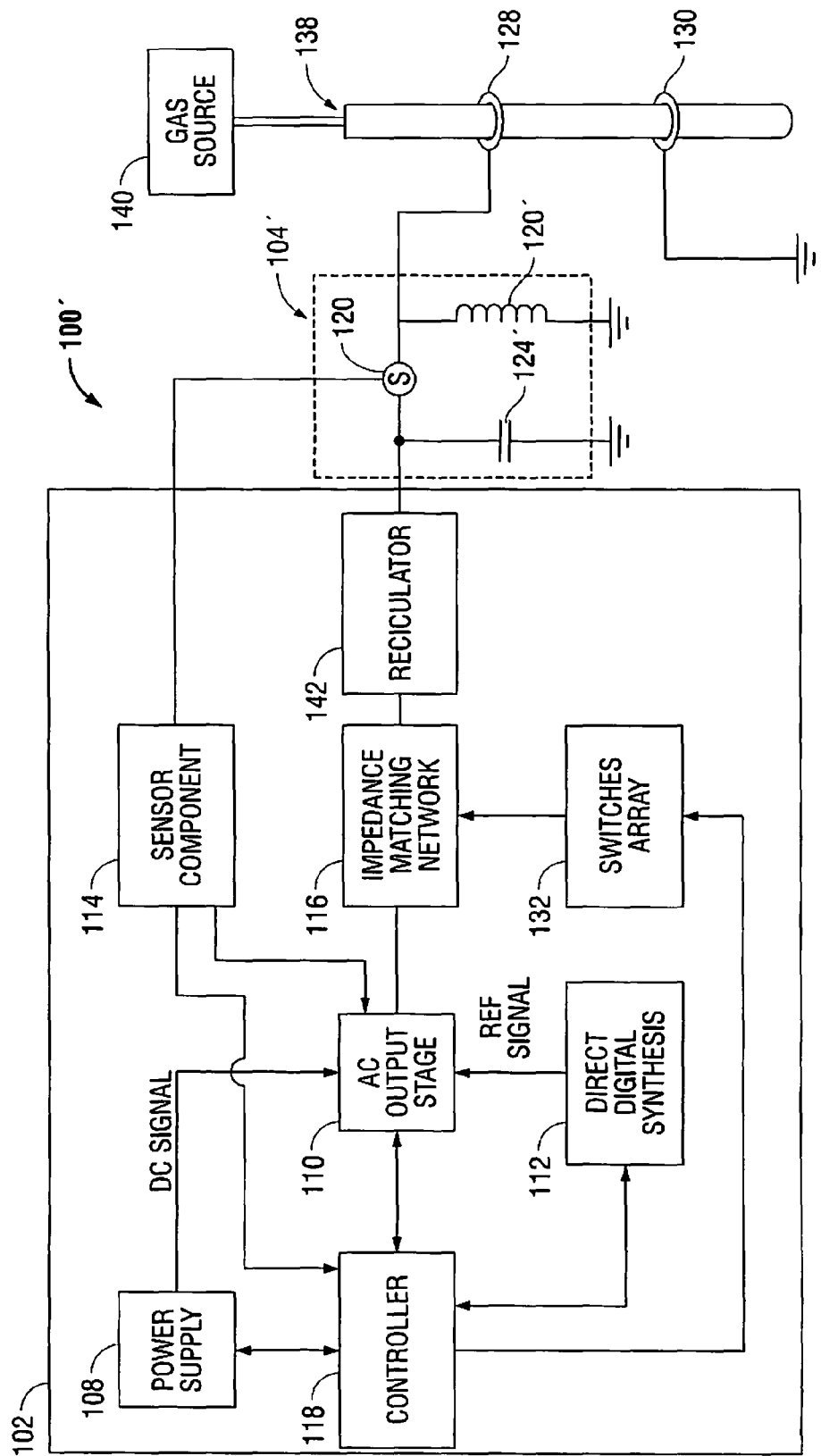
FIG. 1B is a schematic diagram of a plasma generation system in accordance with another embodiment of the present disclosure.

FIG. 1B shows another embodiment of a plasma generation system 100'. Plasma generation system 100' includes an inductor 122' and a capacitor 124' forming resonant circuit 104'. Inductor 122' and capacitor 124' are connected in parallel between isolator 142 and a ground. Isolator 142 prevents the electrical energy from damaging solid-state devices within driver network 102. Isolator 142 may be a circulator, a transformer without windings, or other high voltage protection device. Parallel-resonant circuit 104' of FIG. 1B experiences a "Q-ing up" of the current, rather than the voltage as is seen in a series-resonant circuit 104 of FIG. 1A.

Series Resonant-circuit

Figure 1C:
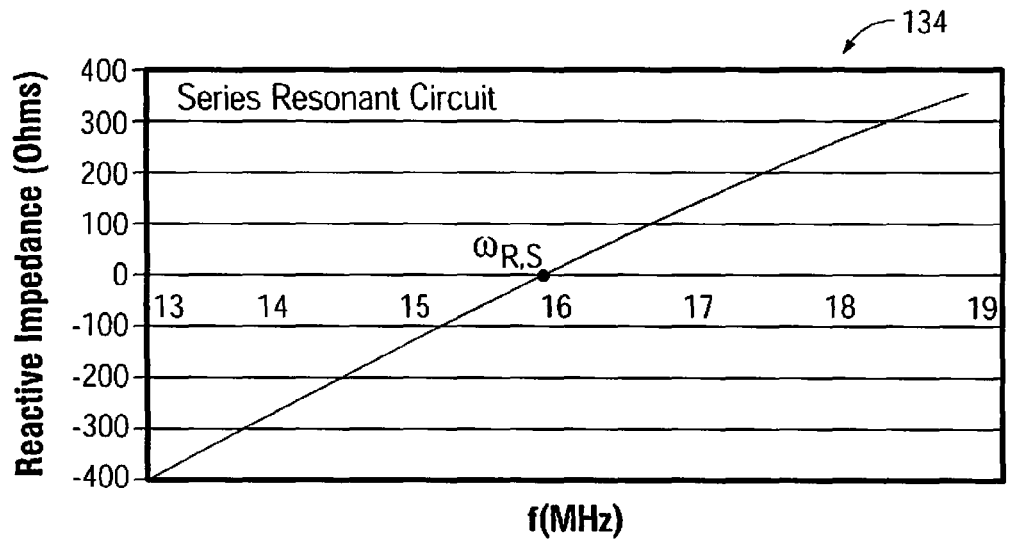
FIG. 1C is a graph of the impedance vs. frequency of the resonant circuit in a series resonant configuration of FIG. 1A in accordance with the present disclosure.
Figure 1D:
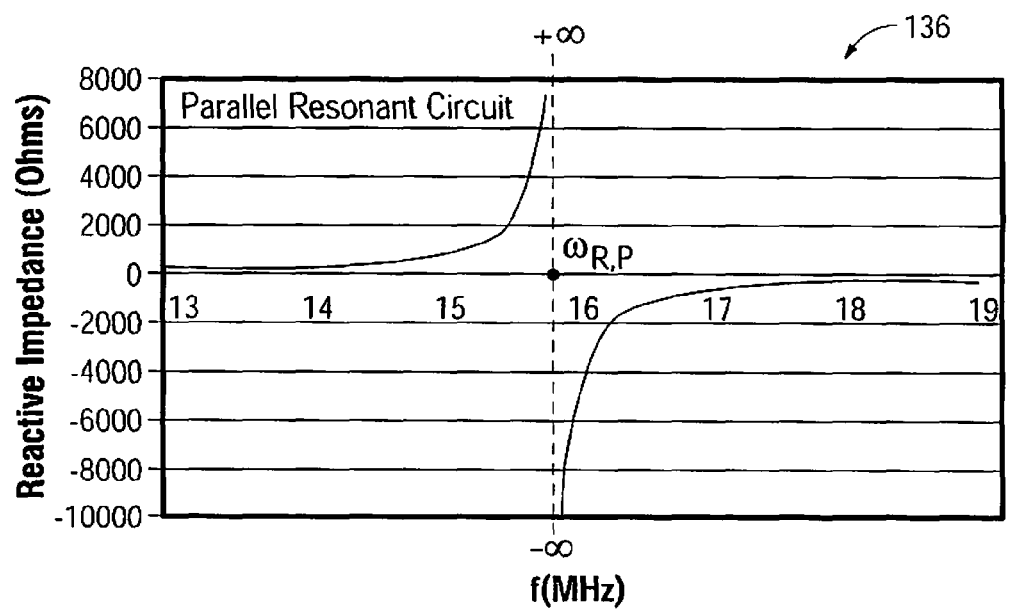
FIG. 1D is a graph of another embodiment of a resonant circuit in a parallel-resonant configuration in accordance with the present disclosure.

Referring to the drawings, FIGS. 1C and 1D show graphics of the impedance of two LC circuits in accordance with an embodiment of the preset disclosure. FIG. 1C shows a graphic 134 of the impedance vs. frequency of the resonant circuit 104 of FIG. 1A. In an exemplary embodiment, resonant circuit 104 of FIG. 1A is in a series-resonant configuration, inductor 122 has a inductor value of 10 microhenries, and capacitor 124 has a value of 10 picofarads resulting in a series-resonant frequency of about 15.92 MHz. The impedance given by resonant circuit 104 of FIG. 1A is shown in Equation (1) as follows:

$$Z = \left(\omega L - \frac{1}{\omega C}\right) j. \tag{1}$$

As shown in FIG. 1C, within a few MHz below and above the series-resonance frequency of $\omega_{R,S}$, the impedance is very linear and is closely bounded to the internal impedance of the sufficiently designed driver circuit 102 of FIG. 1A.

FIG. 1D shows a graphic 136 of the impedance vs. frequency of another embodiment of a resonant circuit in a parallel-resonant configuration as shown in FIG. 1B. FIG. 1D shows the illustrative behavior of a parallel-resonant circuit having an inductor with a value of 10 microhenries and a capacitor with a value of 10 picofarads, resulting in a parallel-resonant frequency $\omega_{R,P}$ of about 15.92 MHz. The impedance of the parallel-resonant circuit is shown in Equation (2) as follows:

$$Z = \frac{1j}{\left(\left(\frac{1}{\omega L}\right) - \omega C\right)}. \tag{2}$$

As shown by graphic 136, when the parallel-resonant LC circuit is driven at parallel resonance frequency of $\omega_{R,P}$, the impedance is very high (e.g., approaching infinity), has a strong variation with frequency that is non-linear, and is discontinuous at $\omega_{R,P}$. As the frequency crosses through the parallel resonance frequency of $\omega_{R,P}$, the phase difference abruptly changes from about +90 degrees to about −90 degree, or visa versa. A parallel-resonant circuit embodiment will experience a "Q-ing up" of the current, rather than the voltage as is seen in a series-resonant embodiment. When the plasma is generated using a parallel-resonant LC circuit, it adds a resistive and capacitive load in parallel to the parallel resonant L and C components thereby dominating net current flow in the circuit. To obtain practical amounts of current in the plasma, the operating frequency and/or plasma capacitance should be sufficiently high, therefore operation at increased frequencies and/or with relatively large electrodes may be required to excite plasma using a parallel-resonant LC circuit. When utilizing an parallel-resonant LC circuit, the voltage developed across the resonant circuit can feed back directly into the power supply which in turn increases the likelihood of overvoltage or over current damage to modern solid-state electronics either on a continuous or transient basis unless sufficient protection devices are used, e.g., an isolator, a circulator, a transformer without windings, other high voltage protection device, and the like.

Referring again to FIG. 1A, circuit theory analysis provides that resonant circuit 104 displays resonant behavior (and thus a resonance frequency) when the AC signal from driver network 102 is at a value $\omega_R$ as shown in Equation (3) as follows:

$$\omega_R = \sqrt{\frac{1}{LC}}, \tag{3}$$

where L is the inductance of inductor 122 and C is the capacitance of capacitor 124. However, note that a load, e.g., a plasma, can change the resonance frequency. In an embodiment of the present disclosure, resonant circuit 104 is driven by AC output stage 110 at a frequency $\omega_R$. As shown in Equation (4) below, resonant circuit 104 has an impedance of:

$$Z = R + jX = R + jX_L - jX_C = R + j\omega L - j(1/\omega C) \tag{4}$$

Non-ideal behavior of a physical inductor and capacitor includes internal resistances, sometimes modeled as Equivalent Series Resistance (ESR) represented by R in Equation (4). The ESR of inductor 122 and capacitor 124 are modeled as zero for simplicity only. It is the purview of one of ordinary skill in the art to model the ESRs of inductor 122 and capacitor 124.

The characteristic impedance of resonant circuit 104 is:

$$|Z| = |ZZ^*|^{1/2} = \sqrt{\frac{L}{C}}. \tag{5}$$

It is noted that the condition of Equation (5) also represents the condition for maximum energy storage in inductor 122 and capacitor 124. Based upon the selection of the L and C values of inductor 122 and capacitor 124, respectively, the solution for the resonant value of $\omega_R$ is trivial utilizing Equation (3) above. However, when the AC signal has a frequency of $\omega_R$, the solution to Equation (4) is Z=0. The solution of Z=0 using Equation (4) results when the AC signal to resonant circuit 104 is at $\omega_R$ because the magnitude of the reactive component of inductor 122, $X_L$ is equal to the magnitude of the reactive component of capacitor 124, $X_C$. Using typically chosen inductor 122 and capacitor 124 values, Equation (5) usually results in |Z| being about 1-10 kΩ; and in some embodiments, the L/C ratio used is from about 500 to 100,000. Note that the "Maximum Power Transfer Theorem" for AC circuits states that to obtain maximum external power from a source with finite internal impedance, the impedance of the load should be matched to the internal impedance, e.g., the source impedance equals the load impedance when both are real, which typically occurs at 50 Ω in high frequency power technology.

Therefore, according to another embodiment of the present disclosure, plasma generation system 100 uses driver network 102 to drive resonant circuit 104 using an AC signal at a near-resonant frequency, $\omega_D$. Resonant circuit 104 when operated at $\omega_D$, a frequency near $\omega_R$ by a factor of $\alpha$, or equivalently shifted $\beta\omega_R$ in frequency (100*$\beta$ percent) is described in Equation (6) as follows:

$$\omega_D = \alpha \omega_R = (1+\beta)\omega_R = \alpha \sqrt{1LC} \tag{6}$$

The reactive component of Equation (4), X=$\omega$L−(1/$\omega$C), of resonant circuit 104 when being driven at near-resonance, $\omega_D$, results in $$X = \omega_D L - (1/\omega_D C) = \tag{7}$$

$$\alpha \omega_R L - (1/\alpha \omega_R C) = \alpha \sqrt{\frac{L}{C}} - \frac{1}{\alpha}\sqrt{\frac{L}{C}} = \sqrt{\frac{L}{C}}\left(\alpha - \frac{1}{\alpha}\right).$$

Equation (7) presents an estimation of the reactive impedance behavior of resonant circuit 104. Equation (7) also accounts for small differences between the calculated resonant frequency of resonant circuit 104 and the actual operation frequency used in practice as driven by the AC signal from driver network 102. At $\alpha$=1, the impedance is zero as derived from Equation (4) above, and at large values of $\alpha$, the impedance of resonant circuit 104 becomes larger than the characteristic impedance as derived from Equation (5) above. Active selection and control of $\alpha$ is a way to control load impedance experienced by AC output stage 110.

The behavior of the total reactive component X of resonant circuit 104 under near-resonant conditions when a is near but not equal to 1 may be shown by choosing a value where $\beta \ll 1$ where $\alpha = 1+\beta$ resulting in Equation (8) as follows:

$$X = 2\beta \sqrt{\frac{L}{C}}. \tag{8}$$

In the embodiment where driver network 102 has an internal impedance of about 50 Ω, Equation (8) provides that driver network 102 may drive resonant circuit 104 at a frequency that is near the resonant frequency $\omega_R$, e.g., such as at a $\omega_D$, to see an equivalent load impedance of resonant circuit 104 of approach about 50 Ω. Therefore, in one embodiment of the present disclosure, driver network 102 drives resonant circuit 104 at a near-resonant frequency $\omega_D$.

Figure 2:
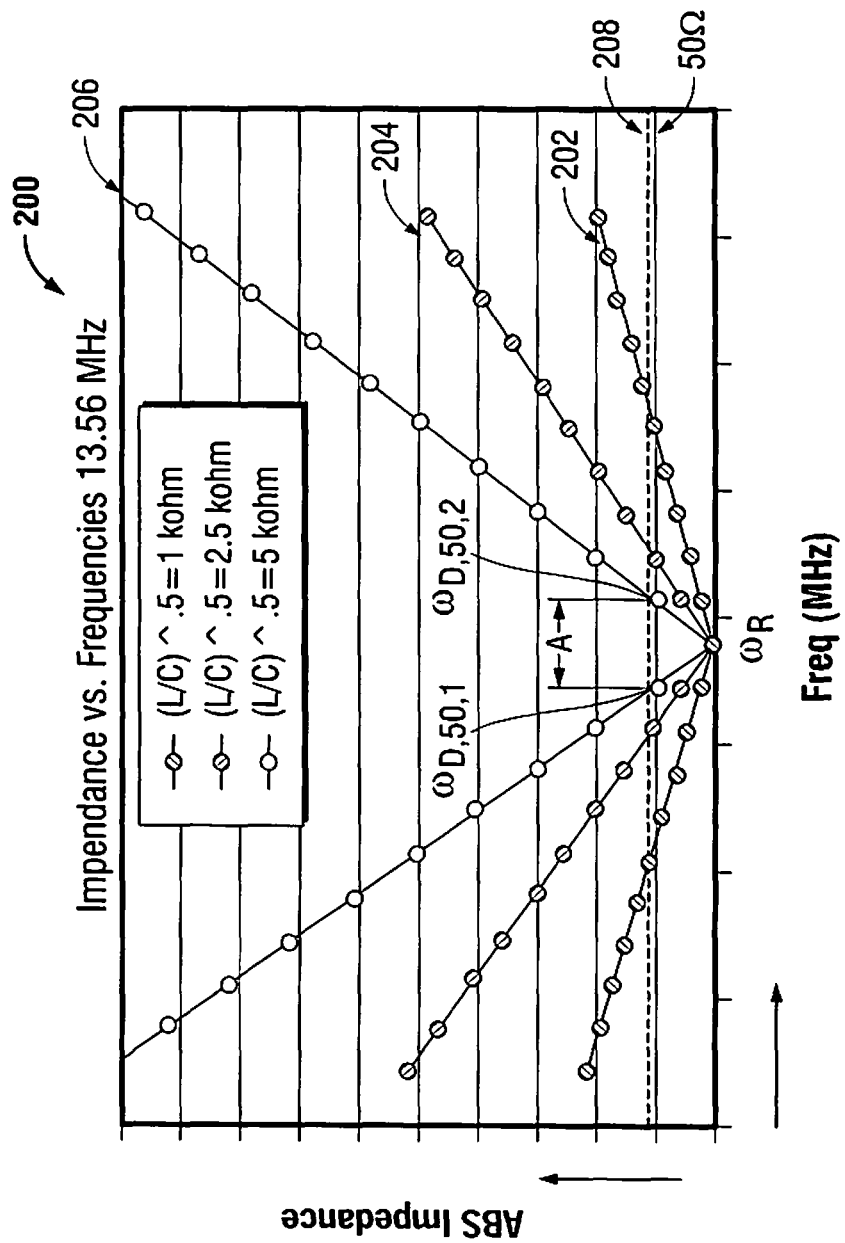
FIG. 2 is a graph showing the effect of varying the excitation AC frequency on the effective impedance of the circuit of FIG. 1A and the source impedance in accordance with the present disclosure.

Referring simultaneously to FIGS. 1 and 2, FIG. 2 shows a graph 200 of the impedance of resonant circuit 104 vs. frequency in several embodiments of the present disclosure. For graph 200, resonant circuit 104 has inductor 122 and capacitor 124 chosen such that resonant circuit 104 forms a 13.56 MHz resonant circuit (see FIG. 1A). Note that the inductive coupling is relatively low in the 10 to 20 MHz range, especially at atmospheric pressures. Graph 200 shows the results of driving the resonant circuit 104 at several frequencies near 13.56 MHz in absolute values of the impedances shown for several exemplary characteristic impedances Z (see Equation (5) above) including the characteristic impedances Z of 1 kΩ, 2.5 kΩ, or 5 kΩ.

Data points 202 show the absolute value of the impedance of resonant circuit 104 where the characteristic impedance is 1 kΩ. Data points 204 show the absolute value of the impedance of resonant circuit 104 where the characteristic impedance is 2.5 kΩ. Data points 206 show the absolute value of the impedance of resonant circuit 104 where the characteristic impedance is 5 kΩ. Data points 208 show the internal impedance of driver network 102, which remains constant at 50 Ω. Note that $\omega_R$ is at 13.56 MHz.

Graph 200 shows that decreasing characteristic impedance requires differences between $\omega_R$ and $\omega_D$ to achieve a 50 Ω value of resonant circuit 104. Alternatively, increasing $\sqrt{L/C}$ requires less of a difference from $\omega_R$ to $\omega_D$, but at the expense of load impedance being more sensitive to frequency.

For example, consider data points 206, which show the absolute value of the impedance of resonant circuit 104 where the characteristic impedance is 5 kΩ. Also consider data points 208 which show the internal impedance of driver network 102. Data points 206 include two frequencies where the internal impedance of 50 Ω is matched to an absolute value of the impedance of resonant circuit 104. These two solutions are marked as $\Omega_{D,50\,\Omega,1}$ and $\omega_{D,50\,\Omega,2}$ and may define a bandwidth "A". Bandwidth "A" may also be defined as the range of frequencies about the resonance frequency of resonant circuit 104 where an internal impedance of the driver network 102 is comparable to an impedance of the resonant circuit 104. When driver network 102 drives resonant circuit 104 at a frequency range roughly bounded by $\omega_{D,50\,\Omega,1}$ or $\omega_{D,50\,\Omega,2}$, the internal impedance is about matched to the load impedance. In alternative embodiments, driver network 102 drives at a frequency within bandwidth "A". Matching as used herein may refer to matching the real part of the internal impedance of driver network 102 to the real part of the effective impedance of resonant circuit 104 in the case where imaginary components may be neglected for simplicity. The effective impedance is the impedance experienced by driver network 102. Additionally or alternatively, matching involves making the effective impedance of resonant circuit 104 such that it is the complex conjugate of the internal impedance of driver network 102. However, note that data points 202 and 204 have different frequency ranges at which resonant circuit 104 is well matched to driver network 102.

Referring again to FIG. 1A, an exemplary embodiment is shown with driver network 102 driving resonant circuit 104 at a near-resonant frequency cop. Assume inductor 122 has an inductance of about 24 μH and capacitor 124 has a capacitance of about 4.7 picofarads, for illustration purposes, resulting in an expected operating frequency of 15.4 MHz. After accounting for from parasitic components, an actual network analyzer measurement may read 14.99 MHz. These values indicate a characteristic impedance of about 2.3 kΩ. When the exemplary circuit is driven by driver network 102 without plasma generation using an IFI amplifier driven by a variable frequency, e.g., an Agilent signal generator, the relative voltage between the inductor 122 and capacitor 124 (the Q-ed voltage) may be measured by a voltage probe of an oscilloscope near, but not touching, node 126. By making the measurement in this manner, the air gap acts as minimal capacitive coupling such that the oscilloscope's L and C do not affect resonant circuit 104 (it also protects the probe and oscilloscope from high power levels).

In practice what is observed using the oscilloscope under power loading conditions is that slight variations vis-à-vis the network analyzer, which most commonly occurs at the higher power ranges, results in a near-resonant frequency that is 200-300 kHz lower than the resonant frequency of resonant circuit 104. Previously, this phenomenon was attributed to near-field effects that become more operative as the power level increases. By applying Equation (6) above using X=50 Ω, the result obtained is of a β of 1.09%, i.e., a shift of 167 kHz from $\omega_R$. Temporal stability of this system is observed to drift which is attributed to the increased Joule heating at $\omega_R$ than at $\omega_D$ within resonant circuit 104 because of the ESRs of inductor 122 and capacitor 124. It is estimated this heating causes inductor 122 to expand along its length, which results in inductor 122 having an increased cross-sectional area. Areal increases in inductor 122's cross-sectional area results in larger inductance values, L, and thereby shifts the resonant frequency of resonant circuit 104 lower. This shift may occur minutes after driving resonant circuit 104 at $\omega_R$, resulting in a re-adjustment of the frequency of the AC signal from driver network 102. Typically, a tunable bandwidth of +/−200 kHz around 13 MHz, or about 3% is observed and utilized.

Figure 3:
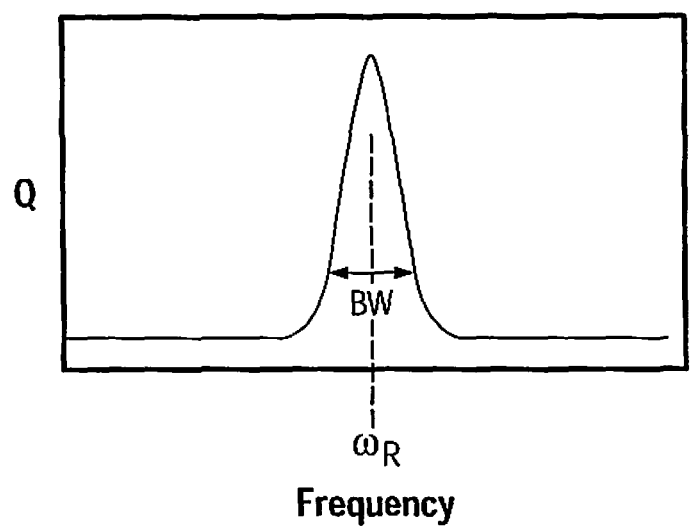
FIG. 3 is a graph showing the behavior of quality factor Q with respect to the changes in the AC driving frequency of the circuit of FIG. 1A for various characteristic impedances in accordance with the present disclosure.

Referring again to FIG. 1A, the resonant condition at $\omega_R$ or near $\omega_R$, such as at $\omega_D$, gives rise to behavior such that the peak voltage present at node 106 is greater than the peak voltage at node 126. The extent to which the voltage at node 126 exceeds the voltage at node 106 may be quantified in various ways. Most conveniently, the ratio of these voltages is expressed by quality factor, Q. That is, resonant circuit 104 "Q's-ups" the voltage at node 126 rather than "Q-ing up" the current. The Q of the circuit can be specified in various equivalent forms, but fundamentally Q represents the reactive impedance, X, of resonant circuit 104 divided by the real impedance, R, of the resonant circuit (Q=X/R). The real impedance results from parasitic resistance or equivalent series resistance (ESR) of the entire circuit. The behavior of Q with respect to frequency is shown in graphical form in FIG. 3, where the Q value peaks at the resonant frequency and there is a corresponding bandwidth where $Q>Q_{max}/2$. The peak in Q is also the frequency at which the voltage that is provided at node 126 in the circuit reaches a maximum. Operation at frequencies within bandwidth "BW" provides resonant excitation. Bandwidth "BW" is 3 dB down from the peak.

Figure 4A:
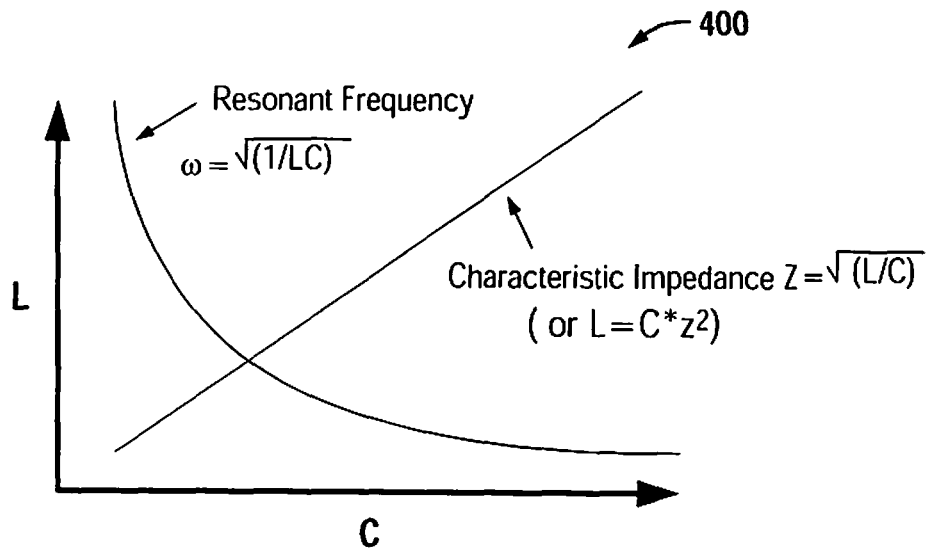
FIG. 4A is a graph showing the two relations of inductance L with respect to capacitance C to simultaneous achieve a resonance or near-resonance frequency at a chosen characteristic impedance, while maximizing the quality factor Q of the circuit of FIG. 1A in accordance with the present disclosure.

Many combinations of capacitor 124 and inductor 122 may be chosen to maximize Q as described above. To further determine the values of capacitor 124 and inductor 122 while $\omega=\sqrt{(1/LC)}$, there exists a secondary condition which maximizes energy content of resonant circuit 104, specifically the condition that characteristic impedance Z of resonant circuit 104 is dominated by the relationship: $Z=\sqrt{(L/C)}$. The parameters of a given plasma source design determines the characteristic impedance Z. A graphic representation of these conditions, which may allow capacitor 124 and inductor 122 to be roughly estimated, is indicated in graph 400 as shown in FIG. 4A.

Figure 4B:
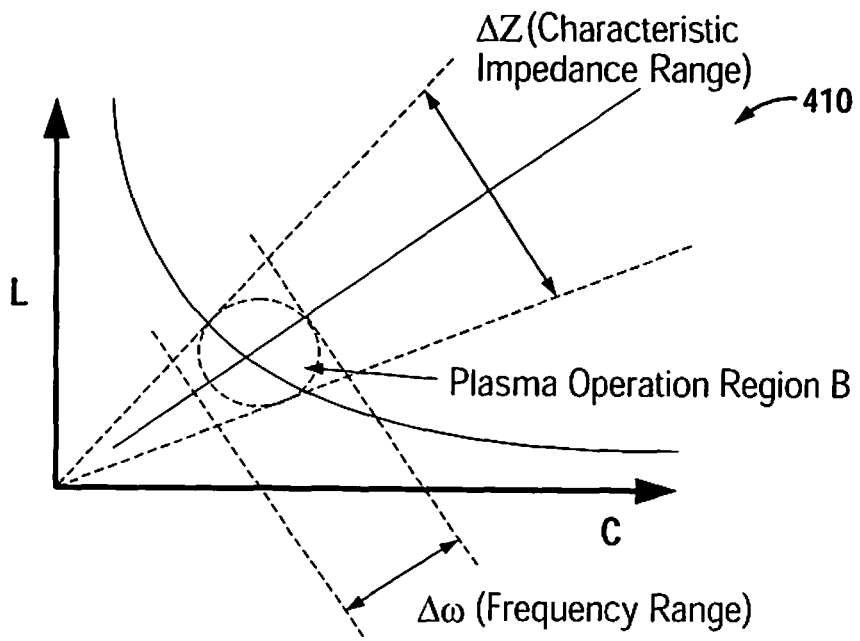
FIG. 4B is a graph of inductance L with respect to capacitance C which indicates the effect on FIG. 4A by changes in resonance frequency and characteristic impedance, and further indicates acceptable ranges of variation in accordance with the present disclosure.

Graph 400 shows a rough estimation where L and C values should be selected for a given frequency and a given characteristic impedance to cause resonant circuit 104 to generate plasma. Current may be controlled and/or applied to maintain the plasma after plasma ignition. When resonant circuit 104 is operated under the conditions of graph 400 the "Q-ed up" voltage of resonant circuit 104 can reach the minimum voltage for plasma ignition to occur. Graph 410 of FIG. 4B provides further insight into practical application of FIG. 4A where changing dynamic conditions necessitates modification of resonant frequency and characteristic impedance. In practice, the changing dynamic conditions cause and require corresponding, but limited, changes in resonant frequency and characteristic impedance. Implementing said limits results in an acceptable plasma operation regime represented in graph 410 as Region "B". The region "B" indicated by the dashed-line around the intersection of the two lines roughly estimates the point of plasma operation that provides both simultaneously sufficient "Q" in the resonant operation range while maintaining the preferred range of characteristic impedances. Region "B" is reached as a function of inductor 122 and capacitor 124 selection using the guidance of FIG. 4A. Once the plasma is ignited, the ESRs of capacitor 124 and inductor 122 increase due to the conductive and capacitive effects of the plasma. This increase in the real impedance of resonant circuit 104 reduces the Q of resonant circuit 104 and the corresponding peak voltage at node 126 applied to the plasma. The plasma excitation voltage may be higher to ignite plasma and lower to sustain the plasma. If the plasma is extinguished, resonant circuit 104 will re-establish a higher effective Q facilitating the re-ignition of the plasma.

Referring to FIG. 1B, resonant circuit 104' is a parallel-resonant circuit and the current is "Q-ed up. "Q-ing up" the current in the parallel-resonant circuit 104' results in a circuit voltage that depends on the impedance of the effective circuit elements. As described earlier, the parallel-resonant embodiment of FIG. 1B may be used with similar criteria for selection of L and C values, but with an additional need to increase both frequency and plasma capacitance. In resonant circuit 104', the developed voltage that excites plasma results in a high "voltage standing wave ratio" (referred to herein as VSWR) experienced by driver network 102'. Modern power supplies are typically rated using a maximum allowable VSWR. Therefore, plasma generation system 100' utilizes circulator 142, but may also utilize isolators, circulators, transformers, and the like.

Referring again to FIG. 1A, plasma generation system 100 includes a controller 118 coupled to sensor component 114. Controller 118 is also coupled to impedance matching network 116. Sensor component 114 receives data from sensor 120. Sensor component 114 is also coupled to AC output stage 110 and is configured to measure reflected and forward power, internal and load impedance. The sensor component 114 may include one or more directional couplers or other voltage and current sensors, which may be used to determine voltage and current measurements as well as the phase difference between the voltage and the current waveforms. The voltage and current measurements are then used by the sensor component 114 to determine the reflected and forward power. The sensor component 114 converts the measured power into corresponding low-level measurement signals (e.g., less than 5V) which are transmitted to the controller 118. Sensor component 114 may include an AD8302 semiconductor or an AD8316 semiconductor, both of which are manufactured by Analog Devices, Inc. of Norwood, Mass.

The controller 118 accepts one or more measurement signals indicative of power delivery, namely the signals indicative of the reflected and forward power, current, voltage and phase difference. The controller 118 analyzes the measurement signals and determines the difference between the reflected and forward power, and/or the input and output impedance. In one embodiment, the measured phase difference between voltage and current may be used to determine an impedance mismatch. In addition, the controller 118 determines the impedance mismatch based on the difference between the reflected and forward power. The controller 118 thereafter determines whether any adjustments to internal impedance of the driver network 102 have to be made to compensate for the mismatch in impedance based on the reflected and forward power measurements. In addition, the controller 118 may also signal the AC output stage 110 and/or the power supply 108 to adjust output power based on the measured impedance mismatch.

Figure 5A:
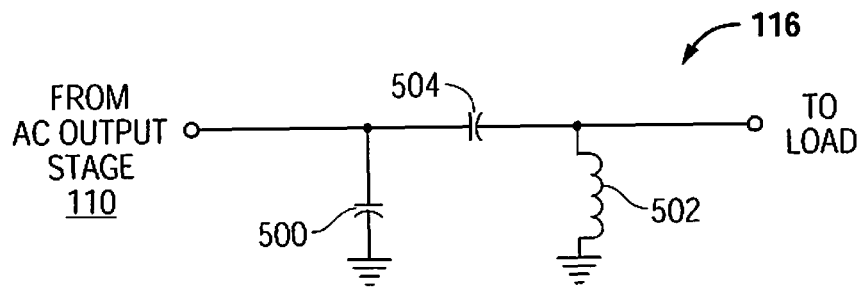
FIGS. 5A to 5D show several embodiments of the impedance matching network of FIG. 1A in accordance with the present disclosure.
Figure 5B:
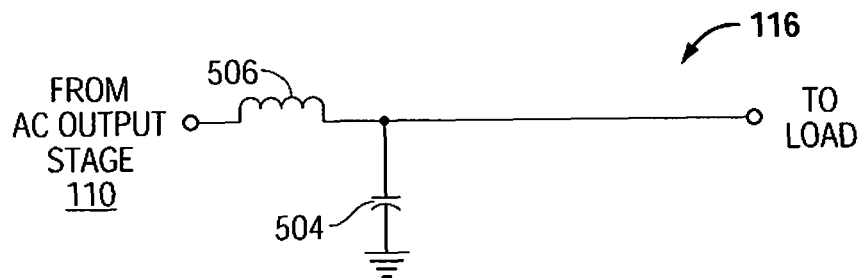
Figure 5C:
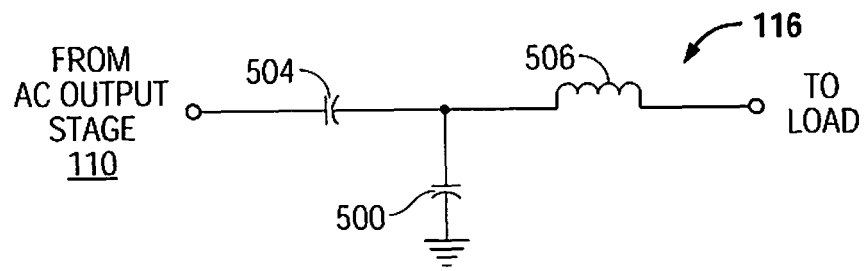
Figure 5D:
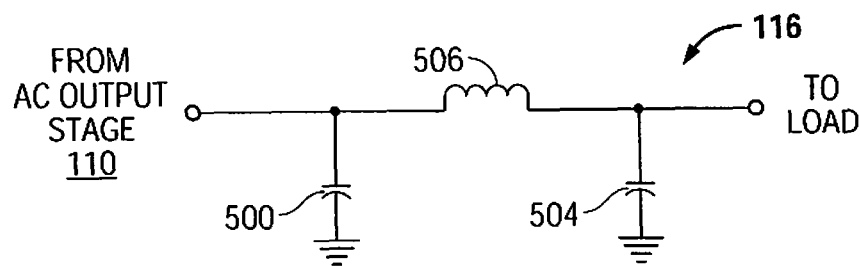

Compensations to the internal impedance of the driver network 102 may be made via a switching array 132 and an impedance matching network 116. The impedance matching network 116 is disposed between the AC output stage 116 and a load (e.g., resonant circuit 104) and includes one or more reactive components such as inductors and capacitors. Embodiments of the impedance matching network are shown in FIGS. 5A-5D. The network 116 includes a shunt capacitance 500 (e.g., provided by a shunt capacitor), a shunt inductance 502 (provided by a shunt inductor) and a tune capacitance 504. FIG. 5A illustrates the network 116 in a "Pi" configuration in which the tune capacitance 504 is disposed between the shunt capacitance 500 and shunt inductance 506. FIG. 5B illustrates the network 116 in an "L" configuration in which the tune inductor 44 is in series and the shunt capacitance 504 is disposed between the AC output stage 116 and ground. FIG. 5C shows the network 116 having the tune capacitance 504 connected in series with an inductance 44 in a "T" configuration in which the shunt capacitance 500 is disposed therebetween. FIG. 5D illustrates the network 116 in a "Pi" configuration in which the inductance 44 is disposed between the capacitances 38 and 40. A suitable configuration of the network 116 may be chosen for the driver network 102 based on the value of the tissue impedance relative to the impedance of the driver network 102.

In one embodiment, the tune capacitance 504 may include two or more switchable reactive components 600 each of which includes a switching element 602 in series with a capacitor 604. Each of the components 600 are in series with AC output stage 116 and the load. Thus, as the AC energy or power from the AC output stage 116 flows through the tune capacitance 504 to the load, the AC energy passes through one or more components 600. In one embodiment, the tune capacitance 504 may include a capacitor, which is in a closed circuit with the AC output stage 116 since at least one circuit path must exist between the AC output stage 116 and the load. In another embodiment, one of the components 600 is activated to provide for a closed circuit between the load and the AC output stage 116.

The switching elements 602 may be either a diode switch, transistor, such as a field-effect transistor ("FET"), insulated-gate bipolar transistor ("IGBT"), or the like, the operation of which is controlled by the switching array 132. In one embodiment, where the switching element 602 is a diode switch, a positive intrinsic negative ("PIN") diode may be used. The switching element 602 may be operated in a variety of modes. The switching elements 602 may be turned "on" for a predetermined amount of time and automatically revert to the open state. In another embodiment, the switching elements 602 may be activated for any desired amount of time. In one embodiment, the switching elements 602 may be RF relays.

The switching array 132 activates and deactivates the switching elements 602 thereby toggling the capacitors 604 in the network 116. The controller 118 signals the switching array 132 to activate and deactivate specific switching elements 602 and specific duration of the activation based on the measured impedance mismatch. More specifically, the controller 118 determines a suitable amount of impedance compensation based on the impedance mismatch as discussed above. To achieve the desired impedance compensation, a predetermined number of the reactive components 600 are activated based on their reactance. The controller 118 then signals the switching array 132 to activate the reactive components 600 to obtain a total reactance of the network 116 that is suitable to compensate for the mismatch in impedance to a specified tolerance. The controller 118 is preprogrammed with the reactive values of individual reactive components 600. In embodiments, the controller 118 may determine which reactive components 600 are activated based on the transmission line equivalents of the reactive components 600 or by using discrete lumped parameter elements. Since the network 116, and, more specifically, the tune capacitance 504, may include any number of reactive components 600, any desired reactance may be established.

Figure 6:
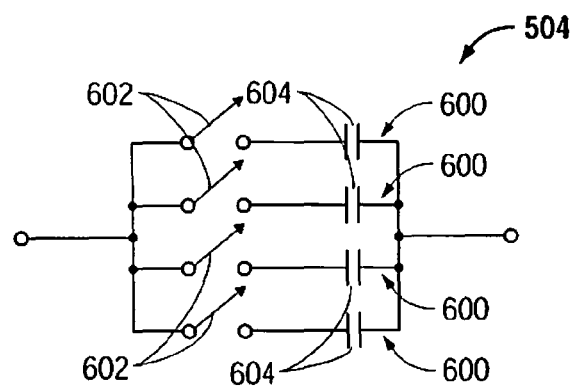
FIG. 6 is a schematic electrical diagram of a switchable tuning capacitance in accordance with the present disclosure.

As shown in FIG. 6, the tune capacitance 504 includes four (4) reactive components 600, which may be of various reactances, thus providing for sixteen (16) different capacitance values. Increasing the number of reactive components 600 to five (5) effectively doubles the number of combinations to thirty two (32). Those skilled in the art will appreciate that any combination of reactive components 600 having any predetermined reactances may be utilized. If the switching elements 602 are diodes or transistors, the switching array 132 may include a diode or transistor push-pull driver circuit (not explicitly shown) which is adapted to activate and deactivate the switching elements 602.

Figure 7:
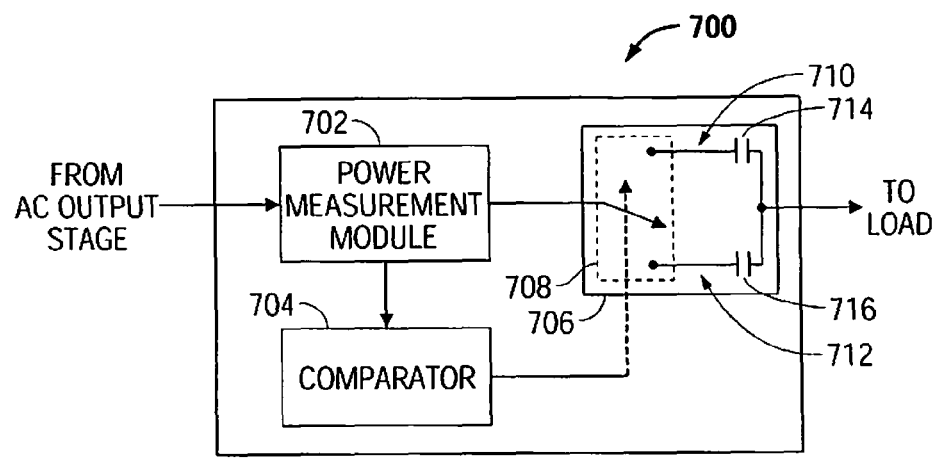
FIG. 7 shows a schematic block diagram of a control system to control the impedance of the impedance matching network of FIG. 1A in accordance with the present disclosure.

FIG. 7 shows a schematic block diagram of a control system 700 for controlling impedance matching network 116. Control system 700 may be part of controller 118, impedance matching network 116, switching array 132 or sensor component 114, or may replace one or more of the same. Control system 700 receives a signal from AC output stage 110 and includes a power measurement module 702 for determining forward power and reflected power. The module 702 also determines the mismatch in impedance based on the measured forward power and the reflected power. The module 702 transmits a measurement signal corresponding to the mismatch in impedance to a comparator 704. In one embodiment, the module 702 may transmit measurement signals representative of the forward and reflected power and/or the difference therebetween to the comparator 704.

The comparator 704 is preprogrammed with a predetermined setpoint representative of maximum mismatched impedance or maximum difference between the forward and reflected power. The comparator 704 compares the difference between measurement signal with the setpoint value. If the measurement signal is less than the setpoint value, the comparator 704 signals a switching assembly 706 to activate a switching element 708 (e.g., diode switch, transistor, or the like) to a first position in which the switching element 708 activates a first reactive component 710. If the measurement signal is larger than the setpoint value, the comparator 704 signals the switching assembly 706 to activate the switching element 708 to a second position to activate a second reactive component 712. The first and second reactive components 710 and 712 include first and second capacitors 714 and 716, respectively. The reactive components 710 and 712 have corresponding first and second reactances such that the first reactance is suitable to compensate for any impedance mismatch when the measurement signal is less than the predetermined setpoint value and the second reactance is suitable to compensate for the impedance mismatch when the measurement signal is larger than the setpoint value. In one embodiment, the setpoint value of the comparator 704 may be set automatically by controller 118 prior to application of the energy. In another embodiment, the setpoint value may be set manually by the user.

Figure 8:
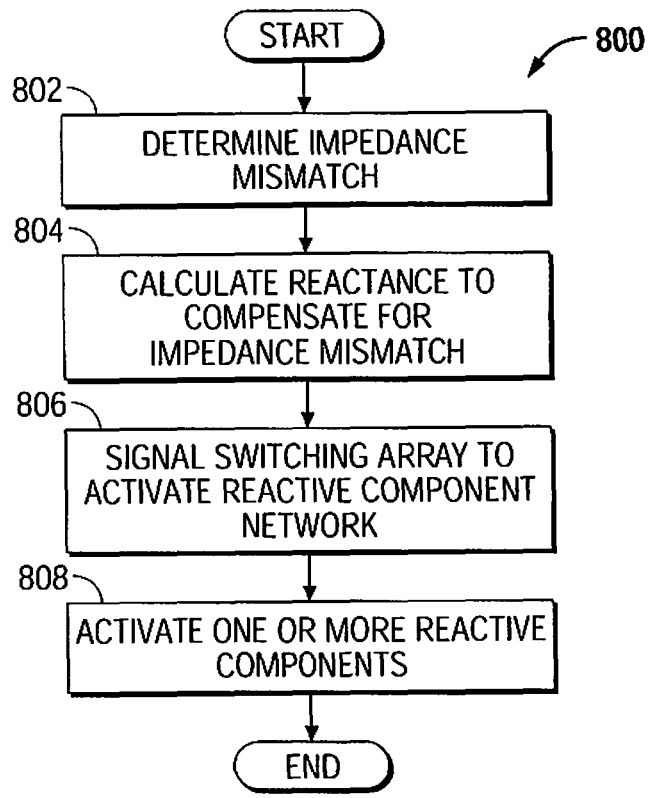
FIGS. 8 and 9 are flow charts illustrating a method for compensating for an impedance mismatch of the plasma generation system of FIG. 1A in accordance with the present disclosure.

FIG. 8 illustrates a method 800 for compensating for an impedance mismatch of the plasma generation system 100 of FIG. 1A in accordance with the present disclosure. In step 802, the plasma generation system 100 determines the impedance mismatch. This may be accomplished by measuring the reflected and forward power along with time or measuring the phase difference as discussed above. The measurement signal representative of the impedance mismatch are transmitted at various time intervals to the controller 118, which then determines the optimum impedance match (if any) between the plasma generation system 100 and the load based on the measurements. In step 804, the controller 118 calculates the reactance to which the impedance matching network 116 should be set to compensate for the impedance mismatch. Since the controller 118 is preprogrammed with the individual reactance values of the reactive components 600 of the impedance matching network 116, the controller 118 determines which of the reactive components 600 should be activated to achieve a desired reactance suitable to compensate for the impedance mismatch. In step 806, the controller 118 signals the switching array 132 to activate reactive components 600 as determined in step 804. In step 808, the switching array 132 provides an activation pulse to the corresponding switching elements 602 of the reactive components 600. Once the switching elements 602 are toggled, the capacitors 604 are connected in series with the AC output stage 110 and compensate for the impedance mismatch. In another embodiment, only the relative reactance is needed and controller 118 increments or decrements added reactance until an acceptable matching condition is obtained.

Figure 9:
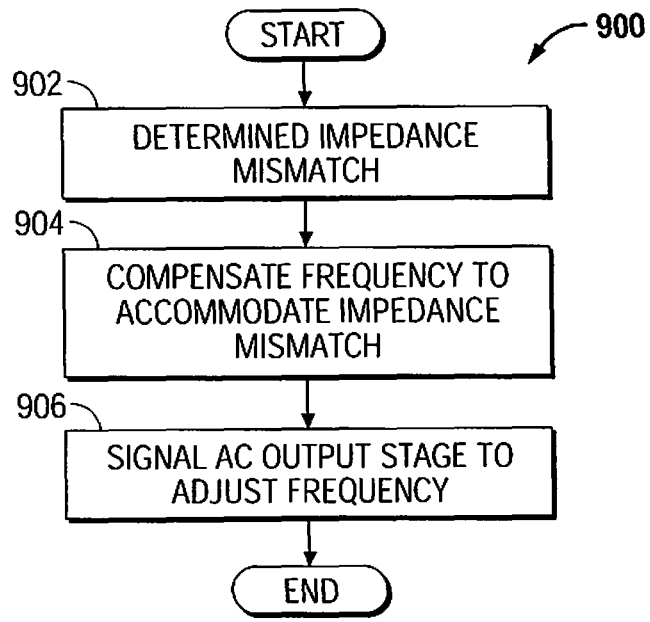

Referring to FIGS. 1 and 9, FIG. 9 illustrates another embodiment of a method 900 of control for an impedance mismatch of the plasma generation system 100 of FIG. 1A, in which the impedance matching network is controlled by tuning the frequency of the AC signal to resonant circuit 104. More specifically, the impedance matching network 116 may be any one of the illustrated embodiments as shown in FIGS. 5A-5D, or no matching network is used. The impedance matching network 116 is constructed by choosing inductance 506 and the capacitances 500 and 504 of predetermined value and then varying the AC signal frequency of the driver network 102 to match the impedance to the resonant circuit 104. Around any particular operational frequency, the impedance matching network 116 has a quasi-linear response for small changes in frequency allowing for precise adjustments in impedance matching. In addition, the impedance matching network 116 may be configured to be sensitive to small changes in the frequency based on component selection and configuration (e.g., selecting a specific CCL circuit). Adjustment to impedance matching by modifying the operational frequency also provides for continuously variable and precise tuning of the impedance (e.g., part-per-billion resolution). In another embodiment, only the relative reactance is needed and controller 118 increments or decrements the frequency until a acceptable matching condition is obtained.

The sensor component 114 determines the impedance mismatch based on reflected power or phase difference, as discussed above. In particular, the sensor component 114 measures the voltage and current supplied to the load. The sensor component 114 may include a log detector, an RMS detector, or a VNA-on-a-chip device. The sensor component 114 then transmits the mismatch impedance to the controller 118, which then adjusts the oscillator frequency of the AC output stage 110 by controlling direct digital synthesis device 112. The controller 118 includes an algorithm m for processing impedance mismatch information to determine frequency adjustments to correct the mismatch. The AC output stage 110 is configured to receive a variable oscillator frequency and is controlled via control signal from direct digital synthesis ("DDS") 112. The AC output stage 110 provides a waveform at a selected frequency that is then amplified for power gain and is applied to the impedance matching network 116 and the load.

In step 902, the sensor component 114 determines the impedance mismatch based on the difference in reflected and forward power or the phase shift as discussed above. In step 904, the measurements reflective of the impedance mismatch are transmitted to the controller 118, which then calculates the adjustments to the frequency, at which the current supplied to the impedance matching network 116 matches the impedance of driver network 102 to resonant circuit 104. In step 906, the driver network 102 applies the RF current at the specified frequency as directed by the controller 118.

Referring to FIGS. 8 and 9, method 800 and 900 may work in conjunction. For example, method 800 may control the impedance matching network such that the frequency applied to resonant circuit 104 remains within a predetermined band, e.g., an ISM band. Thereafter, method 900 may make frequency adjustments only within the predetermined band. Driver network 102 controls the impedance matching network 116 to such that driver network 102 drives resonant circuit 104 at preferred operating parameters and remains within the predetermined band.

Referring again to FIG. 1A, as discussed above, driver network 102 may control impedance matching network 116 and/or the driving frequency of resonant circuit 104 as a function of internal impedance and the impedance of resonant circuit 104. That is, driver network 102 can control for impedance. Additionally or alternatively, driver network 102 may also control the AC signal applied to resonant circuit 104 via node 106 using a phase angle. Sensor 120 may measure and communicate data to sensor component 114. Sensor 120 and sensor component 114, together, can communicate a phase difference between the phase of the current through the plasma and the phase of the voltage across the plasma.

Figure 10:
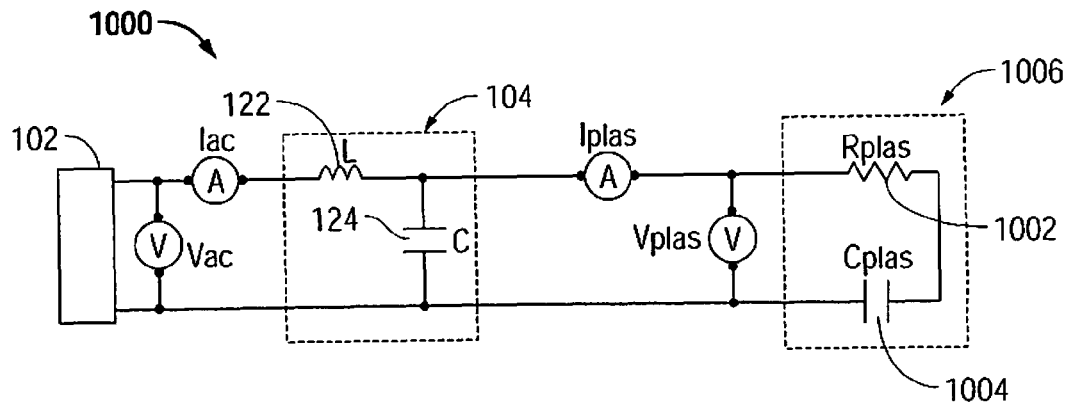
FIG. 10 is an equivalent circuit of the resonant circuit of FIG. 1A, showing the capacitance and resistance contributed by ignited plasma in accordance with the present disclosure.

Referring to FIGS. 1 and 10, FIG. 10 shows a circuit 1000 equivalent to plasma generation system 100 of FIG. 1A. Circuit 1000 shows driver network 102, driving resonant circuit 104 including inductor 122 and capacitor 124. Plasma is shown in circuit 1000 as a lumped-element model including resistor 1002 having a value $R_{plas}$ and a capacitor 1004 having a value $C_{plas}$. The load of the plasma is shown generally as 1006. The voltage and current provided by driver network 102 is shown as $V_{ac}$ and $I_{ac}$, respectively. The voltage and current through plasma is shown as $V_{plas}$ and $I_{plas}$, respectively.

Figure 11A:
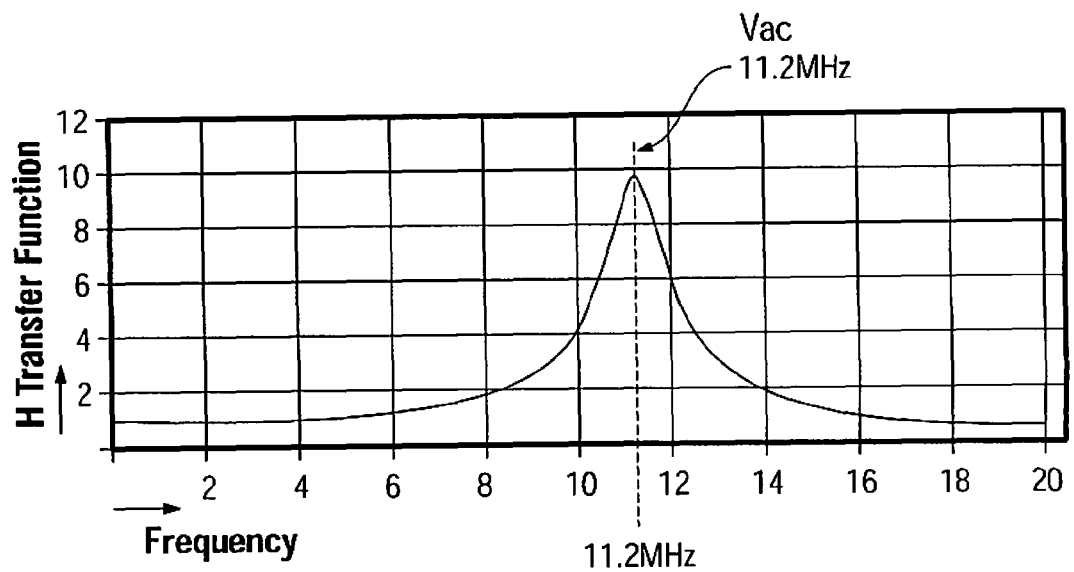
FIGS. 11A and 11B show the effect of controlling the driving frequency of the driver network of FIG. 1 on the phase angle as measured by the sensor of FIG. 1A in accordance with the present disclosure.
Figure 11B:
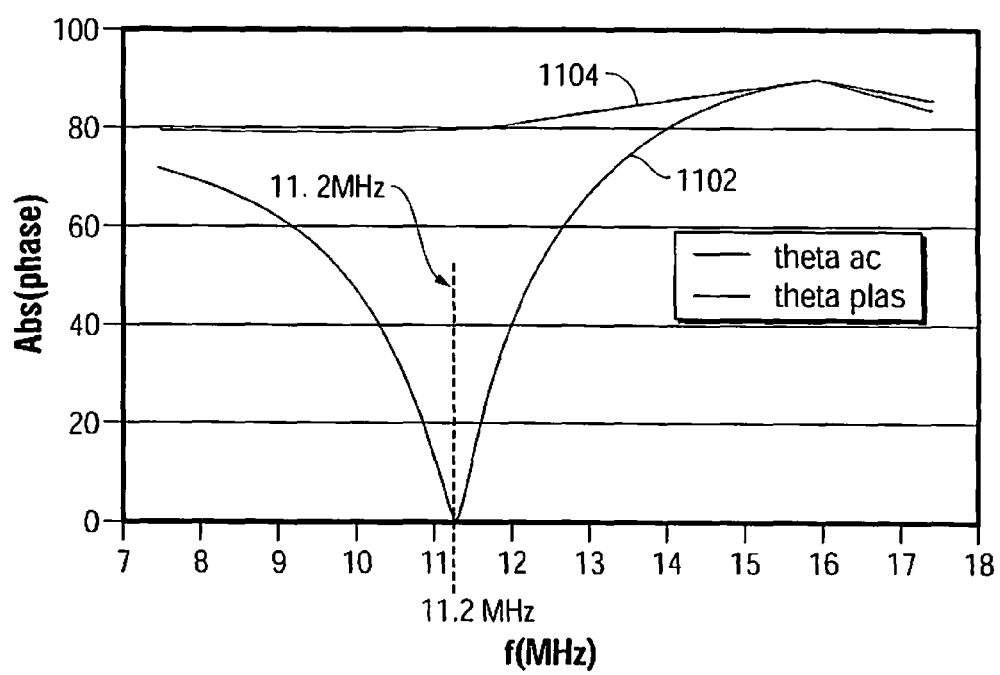

Concerning FIGS. 10, 11A and 11B, control of the resonant circuit 104 may be achieved by controller 118 by controlling delivered power at a chosen frequency. When an AC signal is applied to resonant circuit 102, the load by plasma 1006 includes a resistive component R, shown as $R_{plas}$ and a reactive component X, shown as $C_{plas}$, which in turn leads to a phase difference between Voltage $V_{plas}$ and Current $I_{plas}$ shown by Equation (9) as follows:

$$\theta = \tan^{-1}(X/R) \qquad (9).$$

Additionally, power applied to circuit 1006 is calculated using Equation (10) as follows:

$$\text{Power} = V_{plas} * I_{plas} * \cos\theta \qquad (10).$$

Using the values of $V_{plas}$, $I_{plas}$, (RMS values or peak values may be used) and/or $\theta$ can individually or in some combination thereof be used to control the AC signal applied to resonant circuit 104. Controller 118 may control for voltage, $V_{plas}$, current $I_{plas}$, or phase $\theta$. For example, controller 118 may control on the basis of absolute phase angle $\theta$. It should be noted that, referring to FIG. 11B, the change in phase $\theta$ with frequency may be positive or negative dependent on the operation frequency relative to resonance frequency. Proper design of controller 118 would accommodate this feature. Other improvements to controller 118 could include the ability to preclude the system from transiting the resonance frequency. Additionally or alternatively, the impedance of circuit 1006 or the power applied to 1006 may also be used as a control parameter by controller 118. Controlling for impedance or power introduces additional computation and time delays. Controller 118 can control for a predetermined impedance, or a predetermined impedance range. Controller 118 can control the AC signal to maximize voltage, current, and/or power level.

Referring to FIGS. 11A and 11B, driver network 102 of Fig. 1A can control resonant 104 as a function of a phase difference between the voltage $V_{plas}$ and current $I_{plas}$. In one embodiment of the present disclosure, controller 118 utilizes only phase to control the frequency of the AC signal applied to resonant circuit 104, reducing measurement error, increasing calibration accuracy and enabling the use of Multiple Input Multiple Output technology (referred to herein as "MIMO" and described in more detail below).

Consider the following exemplary embodiment: inductor 122 has a value of 10 microhenries and capacitor 124 has a value of 10 picofarads, resulting in resonant circuit 104 having a resonant frequency of 15.92 MHz. The plasma 1006 modeled by the lumped-elements of resistor 1002 and capacitor 1004 is excited via resonant circuit 104. The effective impedance of plasma 1006 causes a downward shift in the resonant frequency of circuit 1000 to 11.2 MHz as is shown in FIG. 11A. FIG. 11A shows the transfer function H of $V_{plas}/V_{ac}$. Controlling the phase difference between the voltage $V_{plas}$ and current $I_{plas}$, may be implemented by detecting the peak as shown by line 1102 in FIG. 11B. Line 1102 shows the phase difference between the voltage $V_{plas}$ and current $I_{plas}$. Note that the phase difference between $V_{ac}$ and $I_{ac}$ is shown by line 1104 and does not have a correspondingly sharp peak at 11.2 MHz. Controller 118 can control for the phase difference between the voltage $V_{plas}$ and current $I_{plas}$ as shown by line 1102 to achieve a predetermined phase difference. The predetermined phase difference may be about zero or a predetermined value. The measurement of the phase difference between the voltage $V_{plas}$ and current $I_{plas}$ may be achieved, for example, by utilizing an AD8302 semiconductor or an AD8316 semiconductor, both of which are manufactured by Analog Devices, Inc. of Norwood, Mass.

Figure 12:
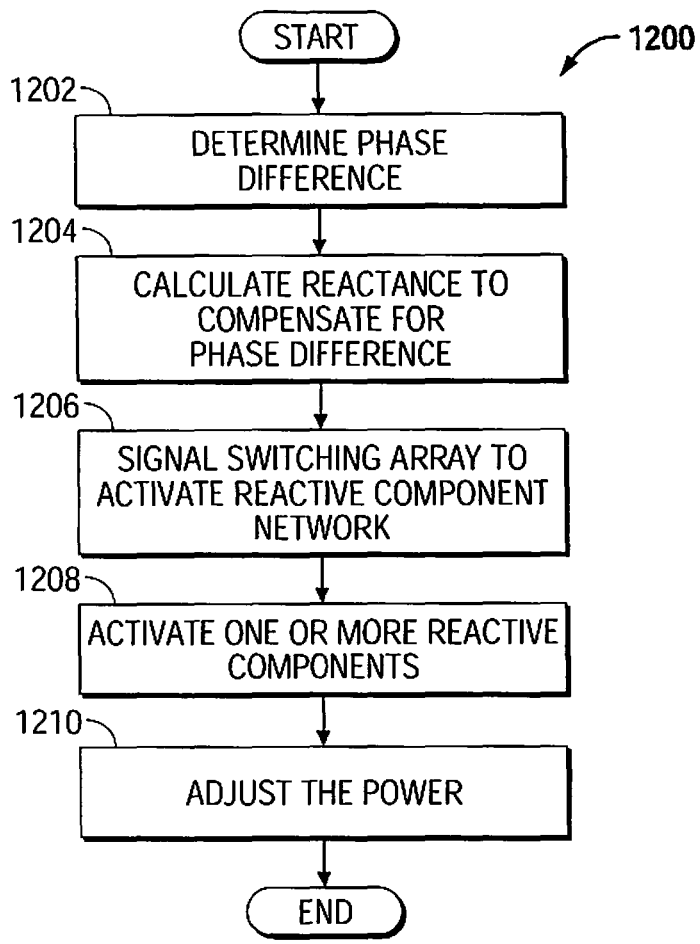
FIGS. 12 and 13 are flow charts illustrating a method of controlling the driver network of FIG. 1 as a function of a determined phase difference as measured by the sensor of FIG. 1A in accordance with the present disclosure.

Referring now to FIGS. 1 and 12, FIG. 12 shows a method 1200 of controlling the driver network 102 of FIG. 1A as at least a function of a determined phase difference as measured by the sensor 120 in accordance with the present disclosure. Method 1200 controls the phase by utilizing impedance matching network 116.

Method 1200 includes steps 1202 through 1210. Step 1202 determines a phase difference between the voltage across the plasma and the current across the plasma, e.g., plasma 1006 as shown in FIG. 10. Step 1204 calculates a reactance, which compensates for the phase difference. Step 1204 calculates a reactance compensation to cause a phase difference being about zero or a predetermined value. Step 1206 signals switching array to activate a reactive component network, e.g., controller 118 signals switching array 132 to control impedance matching network 116. Step 1208 activates one or more reactive components, e.g., the capacitance of 504 shown in FIGS. 5A-5D, and 6 is changed. Step 1210 adjusts the power applied to resonant circuit 104. The power may be adjusted by adjusting the current or voltage from driver network 102.

Figure 13:
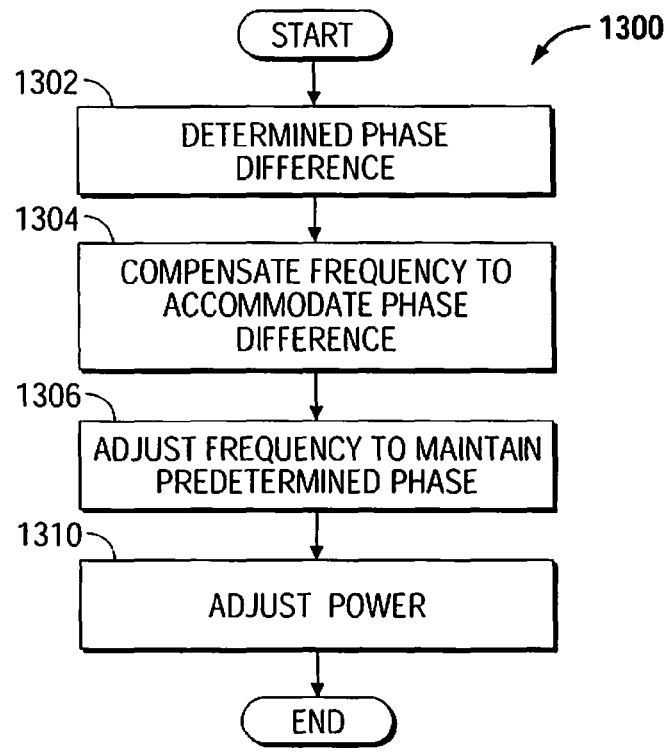

Referring now to FIGS. 1 and 13, FIG. 13 shows a method 1300 of controlling the driver network 102 of FIG. 1A as at least a function of a determined phase difference as measured by the sensor 120 in accordance with the present disclosure. Method 1300 controls the phase by changing the frequency from driver network 102 as applied to resonant circuit 104 via node 106. Method 1300 includes steps 1302 through 1308. Step 1302 determines the phase difference between the voltage across the plasma and the current across the plasma, e.g., plasma 1006 as shown in FIG. 10. Step 1304 compensates frequency to accommodate the phase difference. Step 1306 adjusts the frequency from driver network 102 as applied to resonant circuit 104 to maintain a predetermined phase difference. Controller 118 may adjust the frequency from driver network 102 by controlling the frequency of the reference signal by digitally communicating a phase increment value to a phase increment register of direct digital synthesis device 112. Step 1308 adjusts the power applied to resonant circuit 104. The power may be adjusted by adjusting the current or voltage from driver network 102

Figure 14:
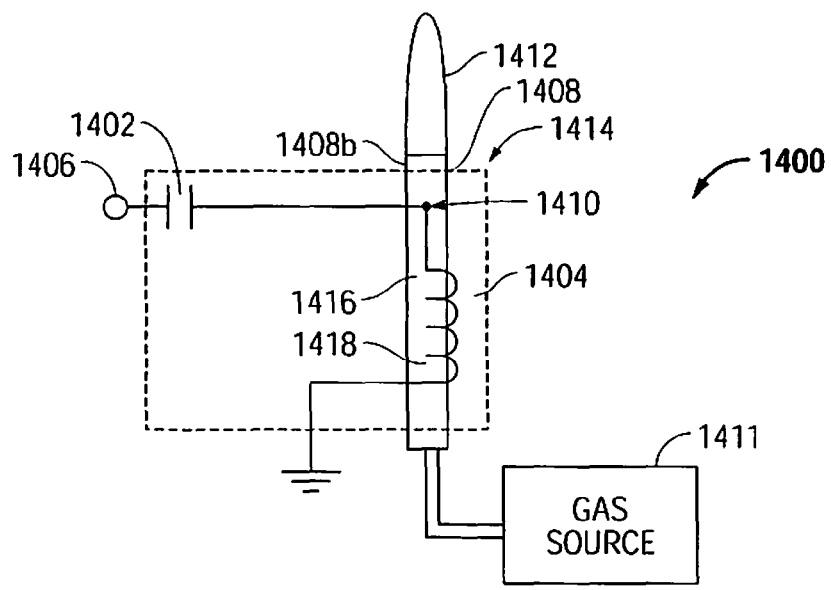
FIG. 14 is a schematic diagram of an embodiment of the present disclosure as including a plasma jet device including the LC circuit and the ignited plasma of FIG. 1A in accordance with the present disclosure.

Turning now to FIG. 14, an embodiment of the present disclosure is illustrated as a plasma generation system, including a plasma-generating device 1400. FIG. 14 operates in a substantially similar manner to system 100 of FIG. 1A, and includes a capacitor 1402, an inductor 1404 and a driver network 1506. The "Q-ed up" high voltage which ignites the plasma appears at node 1410. Capacitor 1402 may include one or more capacitors arranged in various configurations and may include capacitive effects created by the plasma 1412. Capacitor 1402 may be configured with a fixed capacitance or may instead be configured for variable capacitance. Inductor 1404 may include one or more inductors arranged in various configurations. Inductor 1404 may be configured with a fixed inductance or may also instead be configured for variable inductance. As discussed above, capacitor 1402 and inductor 1404 may be interchanged. Additionally, capacitor 1402 and/or inductor 1404 are shown as discrete components, however, capacitor 1402 and/or inductor 1404 may instead be distributed or equivalent components, such as those obtainable in transmission line implementations.

Plasma-generating device 1400 can receive an AC signal from 1406, including any conventional generator or other suitable power source capable of producing an AC signal. Additionally or alternatively, an AC may be received via 1406 from a source identical to or similar to driver network 102 of FIG. 1A. System 1400 further includes a tube 1408. Tube 1408 is a physical structure to limit and/or confine the active plasma volume 1412. Tube 1408 also facilitates confinement of the plasma spatially to a volume isolated from personnel, may be evacuated to a lower pressure to facilitate plasma ignition and operation, and/or facilitates an increase in the purity of the plasma. Additionally or alternatively, tube 1408 may be operated at atmospheric pressures. Tube 1408 may be any suitable geometry that achieves excitation of the ionizable gas from the ionizable gas source 1411. In one embodiment, Tube 1408 is a quartz tube and may have the diameter of a ⅛ of an inch, a ¼ of an inch, or within the range of 2 millimeters to 0.5 millimeters.

Tube 1408 is received within inductor 1404. Inductor 1404 is positioned about tube 1408 such that node 1410 is located near a distal end 1408b of tube 1408. In this manner, the maximum capacitive coupling of the circuit voltage is experienced in distal end 508b of vessel 508 via electrode 1416. Electrode 1416 is electrically coupled to node 1410. Additionally, plasma-generating device 1400 may also include electrode 1418. Electrode 1418 is electrically coupled to a ground. Vessel 508 is connected to a source of ionizable gas source 1411. Ionizable gas source 1411 is controllable to control a temperature rise of a work piece subject to treatment with plasma 1412. During activation of tube 1408, a plasma effluent stream 1412 is emitted from distal end 1410b.

As discussed above, the capacitance C of capacitor 1402 and/or the inductance L of inductor 1404 may be fixed or variable. Capacitor 1402 and inductor 1404 are selected and/or adjusted such that resonant circuit 1414 achieves resonance at a frequency of $\omega_R$ or $\omega_D$, as discussed above. The maximum capacitive coupling of resonant circuit 1414's voltage is experienced at node 1410. Alternatively, the capacitance of capacitor 1402 and the inductance of inductor 1404 may be fixed and the frequency of the power delivered to resonant circuit 1414 may be tuned until $\omega_R$ or $\omega_D$ is achieved. When an input voltage is applied to resonant circuit 1414, if the capacitive coupling of the circuit voltage into the plasma excitation volume (node 1410 in electrical communication with electrode 1416) exceeds a minimum voltage and current, the gas flowing from distal end 1408b of tube 1408 is ignited. Continued application of power to resonant circuit 1414 may sustain plasma generation. The minimum voltage and current necessary to ignite any given gas may be roughly estimated using the Paschen curve. The flow of the gas through tube 1408 may be adjusted as necessary for a given procedure. For example, adjusting the flow of gas may control the temperature induced in a work-piece by plasma 1408b. Using a judiciously chosen capacitor 1402 and inductor 1404 mitigates the need for a dedicated matching network in between the source and the load, although one may still be utilized. One skilled in the art also recognizes that the relatively low capacitance value may be achieved through the inherent capacitance in the metallic electrode 1416, i.e., capacitor 1402 may be all or partly from the capacitance created from electrode 1416. Electrode 1416 may be designed such that there is not need for the literal insertion of a separate or physical capacitive component.

Figure 15:
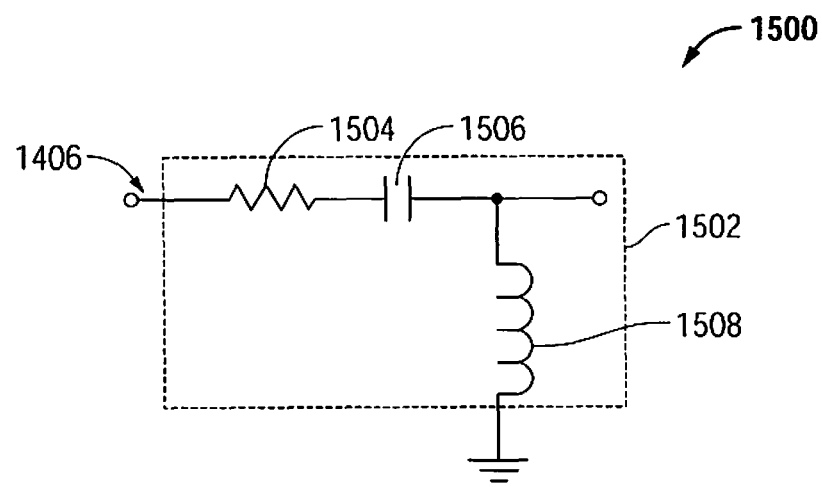
FIG. 15 is a schematic diagram of the LC circuit of FIG. 1A, further including a resistor to control magnitude and frequency dependence of quality factor Q in accordance with the present disclosure.

In practice, it may be difficult to accurately predict the magnitude and behavior of the real part R of the impedance Z of resonant circuit 1414, primarily because of the variability of the plasma conditions. With reference now to FIG. 15, in order to mitigate the problem of accurately predicting the real part R of impedance Z of a resonant circuit, a plasma generation device 1500 includes a resonant circuit 1502 having a resistor 1504 in series with capacitor 1506 and inductor 1508. Resistor 1504 may be fixed or may be a variable resistor. Resistor 1504 has a small resistance, typically below 10 Ω. In resonant circuit 1502, resistor 1504 acts as the dominant source of real impedance R. In practice, the series resistance added by resistor 1504 is generally two (2) to ten (10) times the ESR of capacitor 1506 and inductor 1508, combined.

Figure 16:
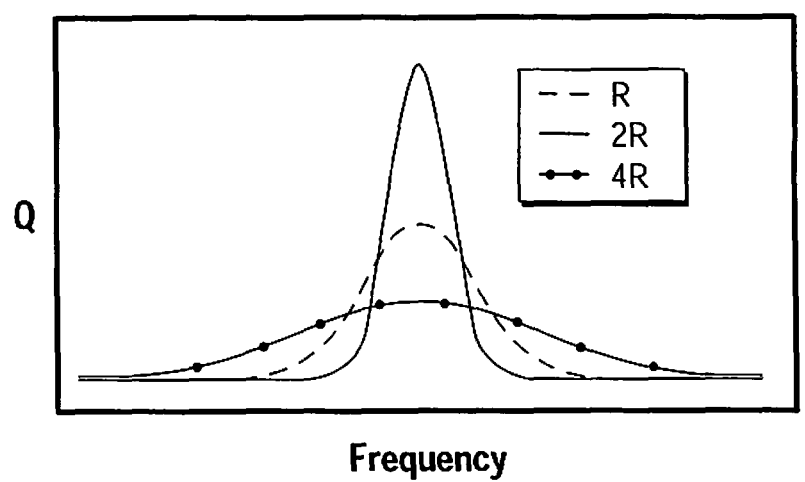
FIG. 16 is a graph showing the effect of the real part R of impedance on quality factor Q with respect to frequency in accordance with the present disclosure.

The addition of resistor 1504 to resonant circuit 1502 has advantages and disadvantages, both of which are evident from the graph shown in FIG. 16. As is shown in FIG. 16, as R is increased, there is a simultaneous decrease in Q and an increase in bandwidth. Thus, the increased R results in a lower developed circuit voltage so power input must be increased to obtain the breakdown voltage for the plasma. The increased R has the beneficial effect of increased bandwidth so changes in plasma conditions have less of a deleterious effect on plasma operation. A narrow bandwidth circuit is typically of limited use because slight perturbations to the plasma will cause the Q-ed voltage to fall below what is required to maintain the plasma. These methods of Q control also may be implemented for L-C-C and C-L-L circuits.

Figure 17:
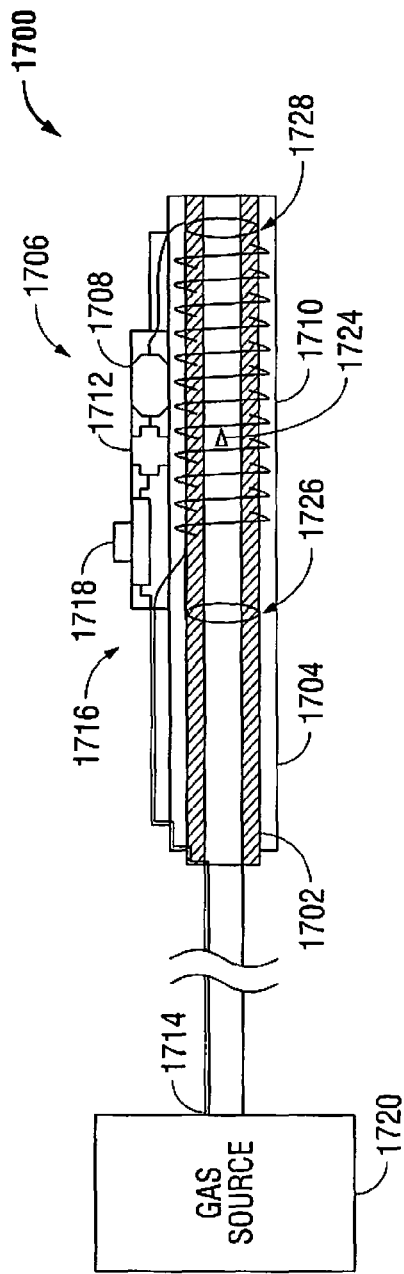
FIGS. 17 and 18 show cross-section side views of an plasma-generating device according to an embodiment of the present disclosure in an unlit or unignited plasma (FIG. 8) as well as in a lit or ignited (FIG. 9) state in accordance with the present disclosure.
Figure 18:
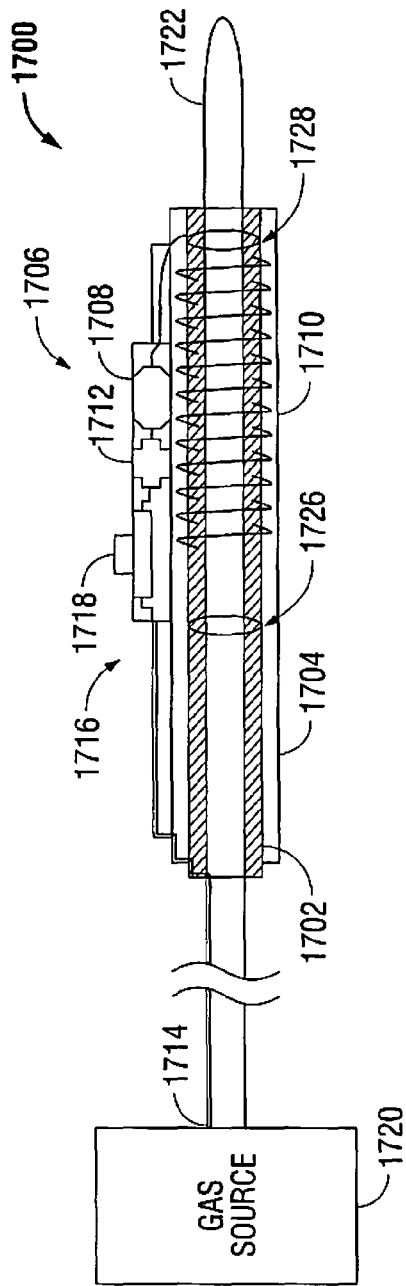

With reference now to FIGS. 17 and 18, an embodiment of a plasma-generating device 1700 according to the present disclosure. Plasma-generating device 1700 includes an inner tube 1702 configured for the passage of ionizable gas and housing 1704 configured to maintain a plasma ignition circuit 1706. Inner tube 1702 and/or housing 1704 may be considered part of the effective impedance of the resonant circuit 1706. In circuit 1706 as shown, inner tube 1702 is composed of an insulating material; however, as will be discussed below, inner tube 1702 does not necessarily need to be insulating. Inner tube 1702 may be a quartz tube. Plasma ignition circuit 1706 is substantially similar to circuit 1502 of FIG. 15 described hereinabove. Circuit 1706 includes a capacitor (or capacitor equivalent) 1708, an inductor (or inductor equivalent) 1710, a resistor (or resistor equivalent) 1712 and an AC power source coming from 1714. One or more of capacitor 1708, inductor 1710 and/or resistor 1712 may be fixed or adjustable, as discussed above. Inductor 1710 produces a magnetic field which does not substantially affect the plasma thereby mitigating the need for shielding; however, it is the purview of one of ordinary skill of the art to utilize such shielding. Plasma-generating device 1700 includes electrodes 1726 and/or 1728. Electrode 1726 may capacitively couple circuit 1706 to an ionizable gas flowing therethrough and electrode 1728 may be grounded to prevent a floating or shifting ground condition. Circuit 1706 further includes an activation mechanism 1716 that includes a button or switch 1718 for activating circuit 1706. Plasma-generating device 1700 is operably connected to a source of ionizable gas 1720.

As discussed above with reference to circuits 104 of FIG. 1A, 1414 of FIG. 14, 1502 of FIG. 15, capacitors 1708, inductors 1710 and resistors 1712 may either be adjusted or selected to maximize Q for a given frequency. Alternatively, the frequency of the power provided to circuit 1706 may be adjusted to maximize Q. Once configured, the plasma jet 1722 of plasma-generating device 1700 may be ignited by activating circuit 1706. Depression of button 1718 causes power to be delivered to circuit 1706 directly as shown or through controls in communication with driver network 102. As discussed above, an increased voltage is experienced in circuit 1706 between capacitor 1708 and inductor 1710. Capacitive coupling of circuit 1706 occurs via electrode 1726. In alternative embodiments, the capacitive coupling can occur downstream near electrode 1728 (or via electrode 1728). Once a minimum voltage and current is achieved, the gas flowing through inner tube 1702 is ignited. Continued activation of circuit 1706 sustains plasma jet 1722 as shown in FIG. 18. A needle electrode 1724 may be electrically connected to circuit 1706 between capacitor 1708 and inductor 1710. Needle electrode 1724 may be selectable connected to circuit 1706 between capacitor 1708 and inductor 1710 (e.g., via a switch, relay, and the like). In another embodiment of the present disclosure, needle electrode 1724 may be intermittently or permanently connected to a ground, e.g., needle electrode 1724 may be connected to a ground to facilitate plasma ignition and then disconnected after ignition of the plasma occurs. In yet another embodiment of the present disclosure, needle electrode 1724 may be intermittently or permanently connected to electrosurgical energy source operating at 472 kHz (e.g., to an electrosurgical energy source as found in electrosurgical generator 2002 of FIG. 10). Needle electrode 1724 extends into distal end 1702*b* of inner tube 1702. Needle electrode 1724 may be included to assist in the ignition of plasma jet 1722.

Figure 19:
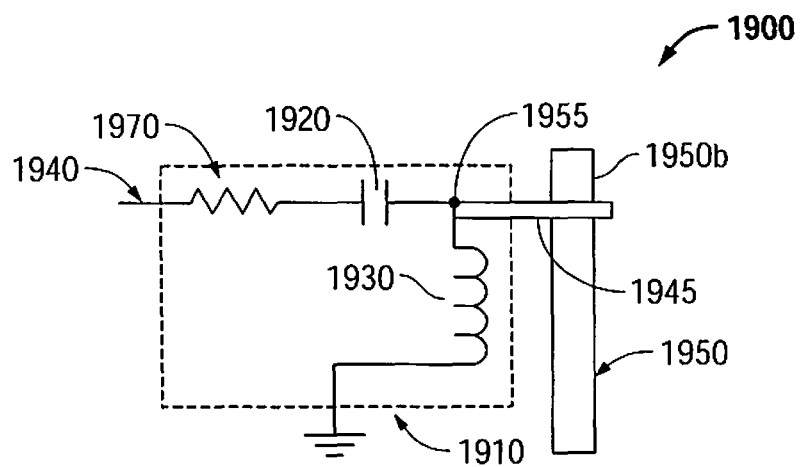
FIG. 19 shows a schematic diagram of another embodiment of the plasma apparatus and resonant circuit in accordance with the present disclosure.

Turning now to FIG. 19, an alternate embodiment of the present disclosure is illustrated as a schematic of an LC series circuit that includes a plasma-generating device laterally spaced from the circuit as shown generally as circuit 1900. LC series circuit 1910 is substantially similar to LC circuit 210 and will only be described as relates to the differences therebetween. LC series circuit 1910 includes capacitor 1920, inductor 1930, resistor 1970 and an AC power source via 1940. LC series circuit 1910 is connected to a plasma generating apparatus 1950 by a strip electrode 1945 or other suitable conductive member such as a coaxial cable. Some other conductive members that may be used include a wire, a waveguide, a metallic strip in a PCB board having a sufficient geometry, a tube of material having a sufficient geometry, and the like. In this manner, the voltage induced at node 1955 in circuit 1910 is also experienced in a distal end 1950*b* of plasma-generating device 1950. Length of distal end 1950*b* to strap 1945 is adjustable to achieve necessary plasma volume for a particular process. As noted above, when a sufficient voltage is achieved in the plasma excitation volume (distal end 1950*b*), the gas exiting distal end 1950*b* of electrosurgical instrument 1950 ignites. In circuit 1910, because inductor 1930 is physically separated from electrosurgical device 1950, there is additional design latitude for designing plasma device 1950, e.g., in some embodiments, the inner tube is not insulating.

Figure 20:
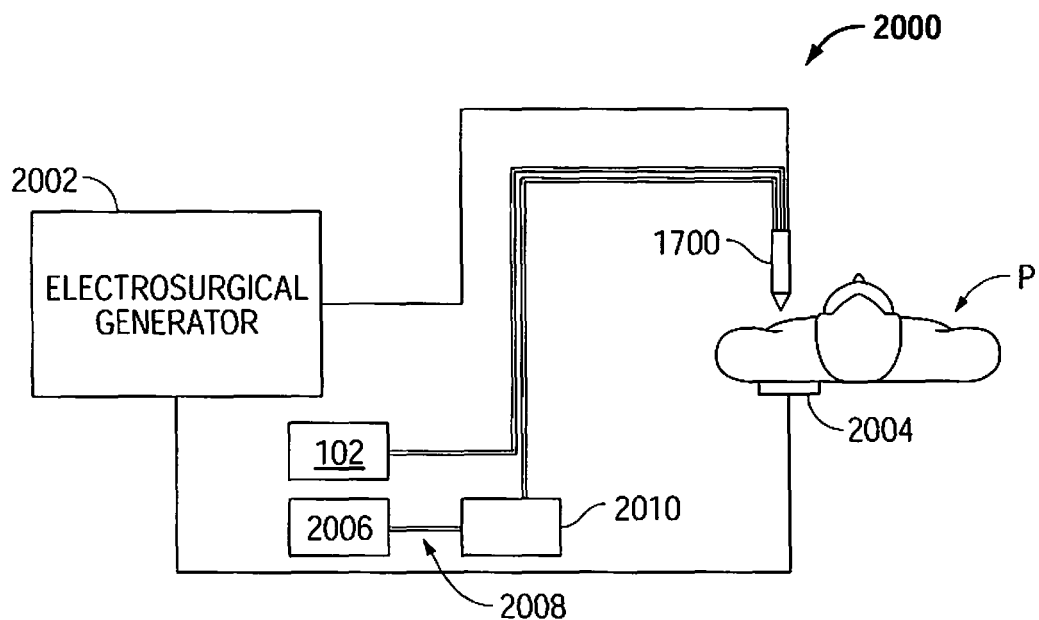
FIG. 20 shows a schematic diagram of an electrosurgical system in accordance with the present disclosure.

Referring to the drawings, FIG. 20 shows a schematic diagram of an electrosurgical system 2000 in accordance with the present disclosure. The electrosurgical generator 2002, according to the present disclosure, can perform monopolar and bipolar electrosurgical procedures, including ablation, coagulation and vessel sealing procedures. The electrosurgical generator 2002 may include a plurality of outputs for interfacing with various electrosurgical instruments (e.g., a monopolar active electrode, return electrode, bipolar electrosurgical forceps, footswitch, smoke evacuator, etc.). Further, the electrosurgical generator 2002 includes electronic circuitry configured for generating radio frequency power and energy levels specifically suited for various electrosurgical modes (e.g., cutting, blending, division, etc.) and procedures.

The generator 2002 according to the present disclosure may be utilized for generating plasma. Electrosurgical system 2000 includes driver network 102. In another embodiment, driver network 102 is part of electrosurgical generator 2002. Additionally or alternatively, the electrosurgical energy generating circuitry may be utilized by a plasma-generating device 1700 to generate plasma.

Driver network 102 ignites a plasma using plasma-generating device 1700. Plasma-generating devices include an active electrode to electrically couple electrosurgical energy from electrosurgical generator 2002 to the plasma. The electrosurgical energy flows through the plasma, through patient P and return to electrosurgical generator 2002 through return pad 2004. The system 2000 may include a plurality of return electrodes 2004 that are arranged to minimize the chances of tissue damage by maximizing the overall contact area with the patient P. In addition, the generator 2002 and the return electrode 2004 may be configured for monitoring so-called "tissue-to-patient" electrical contact resistance to insure that sufficiently low resistance contact exists therebetween to further minimize the chances of tissue damage by unintentional heating. In one embodiment, the active electrode may be used to operate in a liquid environment, wherein the tissue is submerged in an electrolyte solution.

The system 2000 utilizes a plasma-generating device 1700 which may be configured as an electrosurgical pencil coupled to the electrosurgical generator 2002 and an ionizable gas supply 2006. The gas supply 2006 regulates the flow of ionizable gas (e.g., argon, helium, nitrogen) through a tube 2008 to the plasma-generating device 1700 during electrosurgical procedure in conjunction with the supply of electrosurgical energy from the electrosurgical generator 2002. System 2000 may also include a gas cooling device 2010 in fluid communication with and disposed between the source of ionizable gas 2006 and the passage of plasma-generating device 1700. The gas cooling device 2010 is configured to cool the ionizable gas flowing into the passage of the housing of plasma-generating device 1700. The generator 2002 is adapted to provide sufficient energy to ignite the ionizable gas to form the plasma which is then delivered through plasma-generating device 1700 to the treatment site of patient P.

The generator 2002 includes suitable input controls (e.g., buttons, activators, switches, touch screen, etc.) for controlling the generator 2002. In addition, the generator 2002 may include one or more display screens for providing the user with variety of output information (e.g., intensity settings, treatment complete indicators, etc.). The controls allow the user to adjust power or energy of the RF energy, waveform, as well as the level of maximum arc energy allowed which varies depending on desired tissue effects and other parameters to achieve the desired waveform suitable for a particular task (e.g., coagulating, tissue sealing, intensity setting, etc.). The plasma-generating device 1700 may also include a plurality of input controls that may be redundant with certain input controls of the generator 2002. Placing the input controls at the plasma-generating device 1700 allows for easier and faster modification of RF energy parameters during the surgical procedure without requiring interaction with the generator 2002.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A plasma-generating device, comprising:
a housing including a passage defined therein configured to direct a flow of an ionizable gas therethrough;
an electrode in communication with the ionizable gas flowing through the passage of the housing; and
a resonant circuit including a capacitor and an inductor connected together in series, the resonant circuit having a resonance frequency and electrically coupled to the electrode; and
a driver network configured to generate an AC signal having an excitation frequency substantially matching the resonance frequency of the resonant circuit, wherein the driver network provides the AC signal to the resonant circuit to excite the ionizable gas flowing through the passage of the housing to a plasma.

2. The device according to claim 1, further including an insulating tube defining the passage.

3. The device according to claim 2, wherein the electrode is disposed in proximity to the insulating tube.

4. The device according to claim 1, wherein the housing is in fluid communication with a source of the ionizable gas.

5. The device according to claim 4, wherein the electrode is disposed partially upstream adjacent the passage.

6. The device according to claim 1, further including a second electrode coupled to a ground and in communication with the plasma.

7. The device according to claim 6, wherein the housing further includes a fluid connection configured to fluidly connect to a source of ionizable gas to receive the ionizable gas, wherein the second electrode is positioned at an opposite end of a fluid connection.

8. The device according to claim 1, wherein the inductor is formed about the passage within the housing.

9. The device according to claim 1, wherein the electrode has a capacitance connected in parallel to the capacitor.

10. The device according to claim 1, wherein the capacitor and the inductor are connected together in series between the AC signal and a ground.

11. The device according to claim 1, wherein the capacitor has a capacitance value and the inductor has an inductance value, wherein a ratio of the inductance value over the capacitance value is from about 500 square-ohms to about 100,000 square-ohms.

12. The device according to claim 1, wherein at least one of the capacitor and the inductance is adjustable in magnitude.

13. The device according to claim 1, wherein the resonant circuit further includes a resistor electrically coupled to one of the capacitor and the inductor.

14. The device according to claim 13, wherein the resistance of the resistor is about two to about twenty times an equivalent series resistance of the capacitor and the inductor.

15. The device according to claim 1, further including an ignition electrode extending within an end of the housing adapted to assist the ignition of the ionizable gas.

16. The device according to claim 15, further including:
an ignition circuit coupled to the ignition electrode, the ignition circuit adapted to selectively assist in the ignition of the ionizable gas.

17. The device according to claim 16, further including a sensor component adapted to sense a current through the plasma, wherein the ignition circuit assists in the ignition of the ionizable gas when the sensor senses that the current through the plasma is about zero thereby indicating that the resonant circuit is not generating the plasma.

18. The device according to claim 15, further including:
a switch electrically coupled to a driver network providing the AC signal and the ignition electrode, and configured to connect and disconnect the ignition electrode to the driver network.

19. The device according of claim 1, wherein the resonant circuit is electrically coupled to the electrode via a conductive member to communicate electrical energy to the ionizable gas.

20. The device according to claim 1, wherein the resonant circuit is electrically coupled to the electrode via a coaxial cable.

21. The device according to claim 1, further including an electrosurgical electrode adapted to electrically couple electrosurgical energy to the plasma.

22. The device according to claim 1, further comprising:
an impedance matching network electrically coupled between the resonant circuit and a driver network providing the AC signal, the impedance matching network configured to approximately match an internal impedance of the driver network to an effective impedance of at least one of the resonant circuit when exciting the ionizable gas to the plasma and the resonant circuit when not exciting the ionizable gas to the plasma.

23. A plasma generating system, comprising:
a plasma generation device, including:
   a housing including a passage defined therein configured to direct a flow of an ionizable gas therethrough;
   an electrode in communication with the ionizable gas flowing through the passage of the housing; and
   a resonant circuit including a capacitor and an inductor connected together in series, the resonant circuit having a resonance frequency and electrically coupled to the electrode;
a source of ionizable gas in fluid communication with the housing; and
a driver network configured to generate an AC signal having an excitation frequency substantially matching the resonance frequency of the resonant circuit, wherein the driver network provides the AC signal to excite the ionizable gas flowing through the passage of the housing to a plasma.

24. The system according to claim 23, the system further including an impedance matching network electrically coupled between the resonant circuit and the driver network providing the AC signal, the impedance matching network configured to approximately match an internal impedance of the driver network to an effective impedance of at least one of the resonant circuit when exciting the ionizable gas to the plasma and the resonant circuit when not exciting the ionizable gas to the plasma.

25. The system according to claim 23, wherein the circuit further includes a resistor electrically coupled in series with the driver network, wherein the resistor is chosen to decrease a Q and increase a bandwidth of the resonant circuit.

26. The system according to claim 23, wherein the driver network is configured to provide the frequency of the AC signal near to the resonance frequency of the resonant circuit.

27. The system according to claim 26, wherein the driver network provides the frequency of the AC signal to approximately match an internal impedance of the driver network to a predetermined impedance.

28. The system according to claim 27, wherein the predetermined impedance is an effective impedance of the resonant circuit while the resonant circuit generates the plasma.

29. The system according to claim 23, wherein the driver network provides the frequency of the AC signal to maintain a predetermined efficiency of the system.

30. The system according to claim 23, wherein the driver network provides the frequency of the AC signal to maintain a predetermined power dissipation within the plasma.

31. The system according to claim 23, wherein the driver network provides the frequency of the AC signal to maintain a power dissipation within the driver network to be about equal to a power dissipation within the resonant circuit when one of during the generation of the plasma and during no generation of the plasma.

32. The system according to claim 23, wherein the driver network provides the frequency of the AC signal within a predetermined bandwidth.

33. The system according to claim 32, wherein the bandwidth is approximately twice a frequency difference between the resonance frequency of the resonant circuit and another frequency, wherein the another frequency is defined by a frequency such that an internal impedance of the driver network is about matched to an effective impedance of the resonant circuit.

34. The system according to claim 23, wherein the driver circuit is configure to provide the AC signal to excite the ionizable gas to the plasma having an ionization greater than about $1*10^{-7}$.

35. The system according to claim 23, wherein the driver circuit is configured to provide the AC signal to excite the ionizable gas to the plasma having a rotational temperature lower than about 100 degrees Celsius.

36. The system according to claim 23, wherein the driver circuit is configured to provide the AC signal to excite the ionizable gas to the plasma having a rotational temperature lower than about 50 degrees Celsius.

37. The system according to claim 23, wherein the driver circuit is configured to provide the AC signal to excite the ionizable gas to the plasma such that the rotational temperature is substantially lower than the vibration temperature when the plasma is substantially within the passage.

38. The system according to claim 23, wherein the resonant circuit has a Q value sufficient to maintain plasma ignition while dissipating at least one of about 1 watt and about 2 watts within the resonant circuit and the plasma.

39. The system according to claim 23, wherein the driver circuit provides the AC signal such that the AC signal dissipates from about 10's of watts per cubic-centimeter in the plasma to about 1,000's of watts per cubic-centimeter in the plasma.

40. The system according to claim 23, further including:
a gas cooling device in fluid communication with and disposed between the source of ionizable gas and the passage of the housing, the gas cooling device cools the ionizable gas flowing into the passage of the housing.

41. A method of generating plasma, comprising:
providing a fluid path for directing a flow of an ionizable gas;
providing a resonant circuit including a capacitor and an inductor connected together in series, the resonant circuit having a resonance frequency, wherein the resonant circuit is coupled to a driver network configured to supply an AC signal thereto;
determining an excitation frequency of the AC signal to substantially match the resonance frequency of the resonant circuit; and
applying the AC signal to the resonant circuit thereby exciting the ionizable gas to form a plasma.

42. The method according to claim 41, further including:
determining a phase difference between a phase of a current flowing through the plasma and a phase of a voltage across the plasma; and
adjusting the frequency of the AC signal as a function the phase difference.

43. The method according to claim 41, wherein the frequency of the AC signal is adjusted only as a function of the phase difference.

44. The method according to claim 41, further including adjusting the power of the AC signal while maintaining a predetermined phase difference.

45. The method according to claim 41, further including determining an impedance mismatch.

46. The method according to claim 45, further including adjusting the frequency of the AC signal to compensate for the impedance mismatch.

47. The method according to claim 45, further including adjusting an internal impedance of a driver network providing the AC signal to compensate for the impedance mismatch.

48. The method according to claim 41, further including determining a phase difference between a phase of a current flowing through the plasma and a phase of a voltage across the plasma.

49. The method according to claim 48, further including:
comparing the phase difference to a predetermined phase difference; and
adjusting an internal impedance of a driver network providing the AC signal to compensate for the comparison of the phase difference and the predetermined phase difference being greater than a predetermined threshold.

50. The method according to claim 48, further including:
comparing the phase difference to a predetermined phase difference;
adjusting the frequency of the AC signal to compensate for the comparison of the phase difference to the predetermined phase difference; and
maintaining the predetermined phase difference

* * * * *